(12) United States Patent
Humair et al.

(10) Patent No.: US 12,245,935 B2
(45) Date of Patent: Mar. 11, 2025

(54) COMPOSITE WEB-POLYMER HEART VALVE

(71) Applicant: Boston Scientific Limited, Hamilton (BM)

(72) Inventors: Arnaud Humair, Mont-sur-Rolle (CH); Jean-Luc Hefti, Cheseaux-Noréaz (CH)

(73) Assignee: Boston Scientific Limited, Hamilton (BM)

( * ) Notice: Subject to any disclaimer, the term of this patent is extended or adjusted under 35 U.S.C. 154(b) by 328 days.

(21) Appl. No.: 17/094,205

(22) Filed: Nov. 10, 2020

(65) Prior Publication Data
US 2021/0154006 A1 May 27, 2021

Related U.S. Application Data

(60) Provisional application No. 62/940,681, filed on Nov. 26, 2019.

(51) Int. Cl.
*A61F 2/24* (2006.01)
*A61L 27/16* (2006.01)
(Continued)

(52) U.S. Cl.
CPC .......... *A61F 2/2418* (2013.01); *A61F 2/2427* (2013.01); *A61L 27/16* (2013.01);
(Continued)

(58) Field of Classification Search
CPC .................. A61F 2/2418; A61F 2/2427; A61F 2220/0075; A61F 2250/0023;
(Continued)

(56) References Cited

U.S. PATENT DOCUMENTS 4,016,714 A 4/1977 Crandall
4,340,091 A 7/1982 Davis et al.
(Continued)

FOREIGN PATENT DOCUMENTS

AU 2016285561 10/2020
CN 1449266 10/2003
(Continued)

OTHER PUBLICATIONS

"Notice of Allowance," for U.S. Appl. No. 16/413,104 mailed Dec. 24, 2021 (14 pages).
(Continued)

*Primary Examiner* — Brian A Dukert
*Assistant Examiner* — Rebecca Lynee Zimmerman
(74) *Attorney, Agent, or Firm* — Pauly, DeVries Smith & Deffner LLC

(57) ABSTRACT

Embodiments herein relate to polymer coated prosthetic heart valves. In an embodiment, a method of manufacturing a heart valve is included, the method obtaining a frame, attaching a porous web to the frame, applying a coating over at least a portion of the porous web. In an embodiment a heart valve is included. The heart valve including a frame and a plurality of valve leaflets attached to the frame. Each valve leaflet can have a first polymer forming a porous support web and a second polymer forming a coating occluding pores in the porous support web. The valve leaflets can be attached to the frame with a connection structure that is at least partially covered by the coating. Other embodiments are also included herein.

17 Claims, 17 Drawing Sheets

(51) Int. Cl.
*A61L 27/18* (2006.01)
*A61L 27/34* (2006.01)
*A61L 27/56* (2006.01)

(52) U.S. Cl.
CPC ............... *A61L 27/18* (2013.01); *A61L 27/34* (2013.01); *A61L 27/56* (2013.01); *A61F 2220/0075* (2013.01); *A61F 2250/0023* (2013.01)

(58) Field of Classification Search
CPC ...... A61F 2/2415; A61F 2/2412; A61L 27/16; A61L 27/18; A61L 27/34; A61L 27/56; A61L 27/507; A61L 2400/12; A61L 2430/20
See application file for complete search history.

(56) References Cited

U.S. PATENT DOCUMENTS

| | | | |
|---|---|---|---|
| 4,731,074 A | 3/1988 | Rousseau et al. | |
| 4,753,652 A | 6/1988 | Langer et al. | |
| 4,778,461 A | 10/1988 | Pietsch et al. | |
| 5,294,401 A | 3/1994 | Hagiwara | |
| 5,296,292 A | 3/1994 | Butters | |
| 5,476,507 A | 12/1995 | Wakabayashi et al. | |
| 5,674,286 A | 10/1997 | D'Alessio et al. | |
| 5,679,299 A | 10/1997 | Gilbert et al. | |
| 5,688,597 A | 11/1997 | Kohno | |
| 5,740,051 A | 4/1998 | Sanders, Jr. et al. | |
| 5,843,158 A | 12/1998 | Lenker et al. | |
| 6,165,215 A | 12/2000 | Rottenberg et al. | |
| 6,726,715 B2 | 4/2004 | Sutherland | |
| 6,953,332 B1 | 10/2005 | Kurk et al. | |
| 7,335,264 B2 | 2/2008 | Austin et al. | |
| 7,517,353 B2 | 4/2009 | Weber | |
| 7,521,296 B2 | 4/2009 | Wood et al. | |
| 7,615,335 B2 | 11/2009 | Shelnut et al. | |
| 7,786,670 B2 | 8/2010 | Veres et al. | |
| 7,988,900 B2 | 8/2011 | Beith et al. | |
| 8,043,551 B2 | 10/2011 | Heim et al. | |
| 8,324,290 B2 | 12/2012 | Desai et al. | |
| 8,361,144 B2 | 1/2013 | Fish et al. | |
| 8,529,934 B2 | 9/2013 | Desai et al. | |
| 8,590,747 B2 | 11/2013 | Keller | |
| 8,845,580 B2 | 9/2014 | Gellman et al. | |
| 8,864,816 B2 | 10/2014 | Flanagan et al. | |
| 8,945,212 B2 | 2/2015 | Bruchman et al. | |
| 8,975,372 B2 | 3/2015 | Ju et al. | |
| 9,056,006 B2 | 6/2015 | Edelman et al. | |
| 9,074,318 B2 | 7/2015 | Chou et al. | |
| 9,145,627 B2 | 9/2015 | Wilson et al. | |
| 9,205,172 B2 | 12/2015 | Neethling et al. | |
| 9,216,082 B2 | 12/2015 | Von Segesser et al. | |
| 9,255,929 B2 | 2/2016 | Jiang et al. | |
| 9,481,949 B2 | 11/2016 | Zhang et al. | |
| 9,554,900 B2 | 1/2017 | Bruchman et al. | |
| 9,615,919 B2 | 4/2017 | Marissen | |
| 9,737,400 B2 | 8/2017 | Fish et al. | |
| 9,814,572 B2 | 11/2017 | Edelman et al. | |
| 9,944,529 B2 | 4/2018 | Zhang et al. | |
| 9,987,130 B2 | 6/2018 | Weber | |
| 10,195,023 B2 | 2/2019 | Wrobel | |
| 10,299,915 B2 | 5/2019 | Edelman et al. | |
| 10,314,696 B2 | 6/2019 | Wulfman et al. | |
| 10,368,982 B2 | 8/2019 | Weber et al. | |
| 10,413,403 B2 | 9/2019 | Boden et al. | |
| 10,426,609 B2 | 10/2019 | Edelman et al. | |
| 10,433,955 B2 | 10/2019 | Edelman et al. | |
| 10,433,959 B2 | 10/2019 | Levi et al. | |
| 10,716,671 B2 | 7/2020 | Eppihimer et al. | |
| 10,874,843 B2 | 12/2020 | Adenusi et al. | |
| 10,925,998 B2 | 2/2021 | Delaney, Jr. et al. | |
| 11,045,312 B2 | 6/2021 | Flaction et al. | |
| 11,304,798 B2 | 4/2022 | Wulfman | |
| 11,559,394 B2 | 1/2023 | Weber et al. | |
| 12,115,275 B2 | 10/2024 | Delaney et al. | |
| 2001/0025196 A1 | 9/2001 | Chinn et al. | |
| 2002/0082689 A1 | 6/2002 | Chinn | |
| 2003/0055496 A1 | 3/2003 | Cai et al. | |
| 2003/0078652 A1 | 4/2003 | Sutherland et al. | |
| 2003/0097175 A1 | 5/2003 | O'Connor et al. | |
| 2003/0171802 A1 | 9/2003 | Wilder et al. | |
| 2003/0183982 A1 | 10/2003 | Jansen et al. | |
| 2003/0225447 A1* | 12/2003 | Majercak | A61F 2/2475 623/1.13 |
| 2004/0015233 A1 | 1/2004 | Jansen | |
| 2004/0022939 A1 | 2/2004 | Kim et al. | |
| 2004/0088046 A1 | 5/2004 | Speziali | |
| 2004/0122515 A1 | 6/2004 | Chu | |
| 2005/0228486 A1 | 10/2005 | Flagle et al. | |
| 2005/0239508 A1 | 10/2005 | Schwarz et al. | |
| 2006/0171985 A1 | 8/2006 | Richard et al. | |
| 2006/0190074 A1 | 8/2006 | Hill et al. | |
| 2007/0118210 A1* | 5/2007 | Pinchuk | A61L 27/34 623/1.26 |
| 2007/0144124 A1 | 6/2007 | Schewe et al. | |
| 2007/0232169 A1 | 10/2007 | Strickler et al. | |
| 2007/0254005 A1 | 11/2007 | Pathak et al. | |
| 2008/0045420 A1 | 2/2008 | Karagianni et al. | |
| 2009/0041978 A1 | 2/2009 | Sogard et al. | |
| 2009/0054969 A1 | 2/2009 | Salahieh et al. | |
| 2009/0117334 A1 | 5/2009 | Sogard et al. | |
| 2009/0149673 A1 | 6/2009 | Zhang et al. | |
| 2009/0155335 A1 | 6/2009 | O'Shaughnessey et al. | |
| 2009/0324679 A1 | 12/2009 | Ippoliti et al. | |
| 2010/0023104 A1 | 1/2010 | Desai et al. | |
| 2010/0179298 A1 | 7/2010 | Faust et al. | |
| 2010/0249922 A1 | 9/2010 | Li et al. | |
| 2011/0022160 A1 | 1/2011 | Flanagan et al. | |
| 2011/0045030 A1 | 2/2011 | Desai et al. | |
| 2011/0208299 A1 | 8/2011 | Marissen et al. | |
| 2011/0305898 A1 | 12/2011 | Zhang et al. | |
| 2012/0101567 A1 | 4/2012 | Jansen | |
| 2012/0122359 A1 | 5/2012 | Lee et al. | |
| 2012/0172978 A1 | 7/2012 | Dumontelle | |
| 2012/0258313 A1 | 10/2012 | Wen et al. | |
| 2012/0290082 A1 | 11/2012 | Quint et al. | |
| 2013/0150957 A1 | 6/2013 | Weber | |
| 2013/0211508 A1 | 8/2013 | Lane et al. | |
| 2013/0274874 A1 | 10/2013 | Hammer | |
| 2014/0005771 A1 | 1/2014 | Braido et al. | |
| 2014/0005772 A1 | 1/2014 | Edelman et al. | |
| 2014/0018440 A1 | 1/2014 | Boden et al. | |
| 2014/0079758 A1 | 3/2014 | Hall et al. | |
| 2014/0081414 A1* | 3/2014 | Hall | A61L 31/148 264/413 |
| 2014/0088716 A1 | 3/2014 | Zubok et al. | |
| 2014/0163671 A1 | 6/2014 | Bruchman et al. | |
| 2014/0180402 A1 | 6/2014 | Bruchman et al. | |
| 2014/0322512 A1 | 10/2014 | Pham et al. | |
| 2015/0005869 A1 | 1/2015 | Soletti et al. | |
| 2015/0182332 A1 | 7/2015 | Edelman et al. | |
| 2015/0265392 A1 | 9/2015 | Flanagan et al. | |
| 2016/0296322 A1 | 10/2016 | Edelman | |
| 2016/0296323 A1* | 10/2016 | Wulfman | A61L 27/16 |
| 2016/0296325 A1 | 10/2016 | Edelman | |
| 2016/0354201 A1 | 12/2016 | Keogh | |
| 2017/0000610 A1 | 1/2017 | Eppihimer et al. | |
| 2017/0014227 A1 | 1/2017 | Boden et al. | |
| 2017/0071729 A1 | 3/2017 | Wrobel | |
| 2017/0156854 A1 | 6/2017 | Hammer | |
| 2017/0231758 A1 | 8/2017 | Bruchman et al. | |
| 2017/0266350 A1 | 9/2017 | Jiang et al. | |
| 2017/0333185 A1 | 11/2017 | Weber et al. | |
| 2018/0049861 A1* | 2/2018 | Mitchell | A61L 31/041 |
| 2018/0049869 A1 | 2/2018 | Edelman et al. | |
| 2018/0206982 A1 | 7/2018 | Haivatov et al. | |
| 2018/0263765 A1* | 9/2018 | Flaction | A61F 2/2412 |
| 2018/0303972 A1* | 10/2018 | Delaney, Jr. | C08L 53/00 |
| 2019/0125527 A1* | 5/2019 | Binetti | A61F 2/2415 |
| 2019/0262131 A1 | 8/2019 | Wulfman et al. | |

(56) References Cited

U.S. PATENT DOCUMENTS

| | | | |
|---|---|---|---|
| 2019/0350703 | A1 | 11/2019 | Weber et al. |
| 2021/0170069 | A1 | 6/2021 | Delaney, Jr. et al. |
| 2021/0236688 | A1* | 8/2021 | Wagner .................. A61L 27/18 |

FOREIGN PATENT DOCUMENTS

| | | |
|---|---|---|
| CN | 1621424 | 6/2005 |
| CN | 1647777 | 8/2005 |
| CN | 1874799 | 12/2006 |
| CN | 101128225 | 2/2008 |
| CN | 101437663 | 5/2009 |
| CN | 101505723 | 8/2009 |
| CN | 101690683 | 4/2010 |
| CN | 102602083 | 7/2012 |
| CN | 103109330 | 5/2013 |
| CN | 103628147 | 3/2014 |
| CN | 103702636 | 4/2014 |
| CN | 104203151 | 12/2014 |
| CN | 104220104 | 12/2014 |
| CN | 104674578 | 6/2015 |
| CN | 104780952 | 7/2015 |
| CN | 106084094 | 11/2016 |
| CN | 107405426 | 11/2017 |
| CN | 107847321 | 3/2018 |
| CN | 109475409 | 3/2019 |
| CN | 108024857 | 11/2019 |
| CN | 110494170 | 11/2019 |
| CN | 107427366 | 9/2020 |
| CN | 107735052 | 10/2020 |
| EP | 0331345 | 9/1989 |
| EP | 3280357 | 2/2018 |
| EP | 3280358 | 2/2018 |
| EP | 3322382 | 5/2018 |
| EP | 3349693 | 7/2018 |
| EP | 2866847 | 8/2018 |
| EP | 3457989 | 3/2019 |
| EP | 3316818 | 5/2019 |
| EP | 3615097 | 3/2020 |
| JP | S54090897 | 7/1979 |
| JP | S58133318 | 9/1983 |
| JP | H01310659 | 12/1989 |
| JP | 05237140 | 9/1993 |
| JP | H0654868 | 3/1994 |
| JP | 2008531117 | 8/2008 |
| JP | 2011147790 | 8/2011 |
| JP | 2012500074 | 1/2012 |
| JP | 2013502495 | 1/2013 |
| JP | 2013144009 | 7/2013 |
| JP | 2018516610 | 6/2018 |
| JP | 2018516617 | 6/2018 |
| JP | 2018521765 | 8/2018 |
| JP | 2018523503 | 8/2018 |
| JP | 2018527098 | 9/2018 |
| JP | 2020517368 | 6/2020 |
| JP | 6778693 | 10/2020 |
| JP | 6778702 | 10/2020 |
| WO | 0224119 | 3/2002 |
| WO | 02074201 | 9/2002 |
| WO | 2004080346 | 2/2005 |
| WO | 2005039664 | 5/2005 |
| WO | 2006000763 | 1/2006 |
| WO | 2006091382 | 8/2006 |
| WO | 2008097592 | 8/2008 |
| WO | 2009038761 | 3/2009 |
| WO | 2010020660 | 2/2010 |
| WO | 2010048281 | 4/2010 |
| WO | 2014008207 | 1/2014 |
| WO | 2014143866 | 9/2014 |
| WO | 2014149319 | 9/2014 |
| WO | 2014158444 | 10/2014 |
| WO | 2014163795 | 10/2014 |
| WO | 2016025945 | 2/2016 |
| WO | 2016164197 | 10/2016 |
| WO | 2016164209 | 10/2016 |
| WO | 2017004035 | 1/2017 |
| WO | 2017011392 | 1/2017 |
| WO | 2017048575 | 3/2017 |
| WO | 2017200920 | 11/2017 |
| WO | 2018200378 | 11/2018 |
| WO | 2019210059 | 10/2019 |

OTHER PUBLICATIONS

"Second Office Action," for Chinese Patent Application No. 201880024683.0 mailed Dec. 9, 2021 (9 pages) with English Summary.

"Notice of Allowance," for U.S. Appl. No. 16/526,150 mailed Sep. 28, 2022 (12 pages).

"Communication Pursuant to Article 94(3) EPC," for European Patent Application No. 16715724.7 mailed Apr. 15, 2021 (4 pages).

Fazal, Adnan et al., "UHMWPE fibre-based composites: Prestress-induced enhancement of impact properties," Composites Part B, 2014, vol. 66, pp. 1-6 (12 pages).

"International Search Report and Written Opinion," for PCT Application No. PCT/EP2020/083331 mailed Feb. 22, 2021 (12 pages).

"Office Action," for Japanese Patent Application No. 2018-513335 mailed Apr. 6, 2021 (7 pages) with English Translation.

"Second Office Action," for Japanese Patent Application No. 2019-557835 mailed Mar. 9, 2021 (4 pages) with English Translation.

Aksoy, Ayse E. et al., "Surface Modification of Polyurethanes with Covalent Immobilization of Heparin," Macromolecular Symposia, vol. 269, Issue 1, pp. 145-153, Aug. 2008 (9 pages).

Alferiev, Ivan et al., "Prevention of polyurethane valve cusp calcification with covalently attached bisphosphonate diethylamino moieties," J Biomed Mater Res 66A: 385-395, 2003 (11 pages).

Athappan, Ganesh et al., "Influence of Transcatheter Aortic Valve Replacement Strategy and Valve Design on Stroke After Transcatheter Aortic Valve Replacement: A Meta-Analysis and Systematic Review of Literature," J Am Coll Cardiol. 2014;63(20):2101-2110 (10 pages).

Barkoula, Nektaria-Marianthi et al., "Processing of Single Polymer Composites Using the Concept of Constrained Fibers," Polymer Composites, 2005, 26: p. 114-120 (7 pages).

Bastiaansen, Cees W. et al., "Melting Behavior of Gelspun-Drawn Polyolefins," Makromol. Chem., Macromol. Symp., 1989. 28: p. 73-84 (12 pages).

Bates, Frank S. et al., "Multiblock Polymers: Panacea or Pandora's Box?," Science, 2012, 336:434-440 (7 pages).

Berkland, Cory et al., "Controlling surface nano-structure using flow-limited field-injection electrostatic spraying (FFESS) of poly(D,L-lactide-co-glycolide)," Biomaterials (2004) 25: 5649-5658 (10 pages).

Bernacca, Gillian M. et al., "Mechanical and morphological study of biostable polyurethane heart valve leaflets explanted from sheep," J Biomed Mater Res 61:138-145, 2002 (8 pages).

Bhattacharyya, D. et al., "Polyamide 6 single polymer composites," eXPRESS Polym. Lett., 2009. 3(8): p. 525-532 (8 pages).

Cacciola, G. et al., "A Synthetic Fiber-Reinforced Stentless Heart Valve," Journal of Biomechanics, Jan. 1, 2000, pp. 653-658, XP055284947, Retrieved from the Internet: URL:http://ac.els-cdn.com.

Cacciola, G. et al., "A Three-Dimesional Mechanical Analysis of a Stentless Fibre-Reinforced Aortic Valve Prosthesis," Journal of Biomechanics, Jan. 1, 2000, pp. 521-530, XP055284955, Retrieved from the Internet: URL:http://ac.els-cdn.com.

Charles, Lyndon F. et al., "Self-reinforced composites of hydroxyapatite-coated PLLA fibers: fabrication and mechanical characterization," J. Mech. Behav. Biomed. Mater., 2013. 17: p. 269-277 (9 pages).

Claiborne, Thomas E. et al., "In Vitro Evaluation of a Novel Hemodynamically Optimized Trileaflet Polymeric Prosthetic Heart Valve," Journal of Biomechanical Engineering 2013, vol. 135 (8 pages).

De Yoreo, James J. et al., "Principles of Crystal Nucleation and Growth," Biomineralization, Mineral Soc. Am., Washington, DC, 2003, pp. 57-93 (37 pages).

"Decision of Final Rejection," for China Patent Application No. 201380044842.0, mailed Apr. 7, 2017 (18 pages) with Summary.

(56) References Cited

OTHER PUBLICATIONS

"Decision of Rejection," for Chinese Patent Application No. 201380044842.0 mailed Sep. 17, 2019 (9 pages) with English Summary.
Dencheva, Nadya et al., "Structure-properties relationship in single polymer composites based on polyamide 6 prepared by in-mold anionic polymerization," J. Mater. Sci., 2013. 48(20): p. 7260-7273 (14 pages).
Duhovic, Miro P. et al., "Polyamide 66 polymorphic single polymer composites," Open Macromol. J., 2009. 3: p. 37-40. (4 pages).
Fabreguette, et al., "X-ray mirrors on flexible polymer substrates fabricated by atomic layer deposition," Thin Solid Films 515: 7177-7180 (2007), 5 pages.
Fabreguette, Francois H. et al., "Ultrahigh x-ray reflectivity from W/Al2O3 multilayers fabricated using atomic layer deposition," Applied Physics Letters 88: 013166 (2006), 3 pages.
Fakirov, Stoyko "Nano- and Microfibrillar Single-Polymer Composites: A Review," Macromol. Mater. Eng., 2013. 298(1): p. 9-32 (24 pages).
Feng, Yakai et al., "Surface modification of polycarbonate urethane by covalent linkage of heparin with a PEG spacer," Transactions of Tianjin University, Feb. 2013, vol. 19, Issue 1, pp. 58-65 (8 pages).
File History for U.S. Appl. No. 15/595,176 downloaded Feb. 11, 2021 (260 pages).
File History for U.S. Appl. No. 15/959,894 downloaded Feb. 11, 2021 (315 pages).
File History for U.S. Appl. No. 14/656,044 downloaded Feb. 12, 2021 (515 pages).
File History for U.S. Appl. No. 15/797,394 downloaded Feb. 12, 2021 (294 pages).
File History for U.S. Appl. No. 13/932,968 downloaded Feb. 12, 2021 (311 pages).
File History for U.S. Appl. No. 15/082,239 downloaded Feb. 12, 2021 (319 pages).
File History for U.S. Appl. No. 16/413,104 downloaded Feb. 12, 2021 (187 pages).
File History for U.S. Appl. No. 15/082,382 downloaded Feb. 12, 2021 (262 pages).
File History for U.S. Appl. No. 15/082,293 downloaded Feb. 12, 2021 (229 pages).
File History for U.S. Appl. No. 15/193,794 downloaded Feb. 12, 2021 (431 pages).
File History for U.S. Appl. No. 15/205,098 downloaded Feb. 12, 2021 (276 pages).
File History for U.S. Appl. No. 15/257,211 downloaded Feb. 12, 2021 (233 pages).
File History for U.S. Appl. No. 16/526,150 downloaded Feb. 12, 2021 (118 pages).
File History for European Patent Application No. 13739321.1 downloaded Feb. 15, 2021 (377 pages).
File History for European Patent Application No. 16715218.0 downloaded Feb. 15, 2021 (245 pages).
File History for European Patent Application No. 16715724.7 downloaded Feb. 15, 2021 (251 pages).
File History for European Patent Application No. 16736720.0 downloaded Feb. 15, 2021 (256 pages).
File History for European Patent Application No. 16741492.9 downloaded Feb. 15, 2021 (217 pages).
File History for European Patent Application No. 16766455.6 downloaded Feb. 15, 2021 (249 pages).
File History for European Patent Application No. 17725140.2 downloaded Feb. 15, 2021 (119 pages).
File History for European Patent Application No. 18723271.5 downloaded Feb. 15, 2021 (122 pages).
"First Examination Report," for Australian Patent Application No. 2016285561 mailed Mar. 12, 2020 (3 pages).
"First Office Action," for Chinese Patent Application No. 201380044842.0 mailed Dec. 18, 2015 (15 pages) with English Translation.
"First Office Action," for Chinese Patent Application No. 20160036250.8 mailed Nov. 2, 2018 (11 pages) with English Summary.
"First Office Action," for Chinese Patent Application No. 201680018663.3 mailed Mar. 16, 2020 (12 pages) with English Summary.
"First Office Action," for Chinese Patent Application No. 201680018700.0 mailed Nov. 2, 2018 (12 pages) with English Summary.
"First Office Action," for Chinese Patent Application No. 201680040898.2 mailed Feb. 28, 2019, 17 pages, with English summary.
"First Office Action," for Chinese Patent Application No. 201680053293.7 mailed Mar. 5, 2019 (7 pages) with English Summary.
"First Office Action," for Chinese Patent Application No. 201780042303.1 mailed Mar. 26, 2020 (16 pages) with English Summary.
Gallocher, "Durability Assessment of Polymer Trileaflet Heart Valves," FIU Electronic Theses and Dissertations, Paper 54, 2007 (237 pages).
Généreux, Philippe et al., "Vascular Complications After Transcatheter Aortic Valve Replacement: Insights from the PARTNER Trial," J Am Coll Cardiol. 2012;60(12):1043-1052 (10 pages).
George, "Final Report—Fabrication of Nanolaminates with Ultrathin Nanolayers Using Atomic Layer Deposition: Nucleation & Growth Issues," AFOSR Grant No. FA9550-01-1-0075 Feb. 2009 (36 pages).
"Glycosaminoglycan," Wikipedia, posted on or before Oct. 16, 2004, retrieved Feb. 13, 2014, http://en.wikipedia.org/wiki/Glycosaminoglycan, 6 pages.
Gong, Ying et al., "Polyamide single polymer composites prepared via in situ anionic polymerization of ε-caprolactam," Composites, Part A, 2010. 41A(8): p. 1006-1011 (6 pages).
Gong, Ying et al., "Single polymer composites by partially melting recycled polyamide 6 fibers: preparation and characterization," J. Appl. Polym. Sci., 2010. 118(6): p. 3357-3363 (7 pages).
Goyal, R. K. et al., "High performance polymer composites on PEEK reinforced with aluminum oxide," J. Appl. Polym. Sci., 2006. 100(6): p. 4623-4631 (9 pages).
Groner, M. D. et al., "Gas Diffusion Barriers on Polymers Using Al2O3 Atomic Layer Deposition," Applied Physics Letters 88, 051907, 2006 (3 pages).
Han, Dong K. et al., "In vivo biostability and calcification-resistance of surface-modified PU-PEO-SO3," Journal of Biomedical Materials Research, vol. 27, 1063-1073, 1993 (11 pages).
Hass, D. D. et al., "Reactive vapor deposition of metal oxide coatings," Surface and Coatings Technology 146-147 (2001) 85-93, 9 pages.
Hine, P.J. et al., "High stiffness and high impact strength polymer composites by hot compaction of oriented fibers and tapes.," in Mechanical Properties of Polymers Based on Nanostructure and Morphology, CRC Press, 2005 (45 pages).
Hine, P.J. et al., "Hot compaction of woven nylon 6,6 multifilaments," J. Appl. Polym. Sci., 2006. 101(2): p. 991-997 (7 pages).
Hine, P.J. et al., "Hot Compaction of Woven Poly(ethylene terephthalate) Multifilaments," J. Appl. Polym. Sci., 2004. 91(4): p. 2223-2233 (11 pages).
Hine, P.J. et al., "Hybrid carbon fibre/nylon 12 single polymer composites," Composites Part A: Applied Science and Manufacturing 65 (2014) (17 pages).
"International Preliminary Report on Patentability," for International Application No. PCT/US2013/048976 mailed Jan. 6, 2015 (9 pages).
"International Preliminary Report on Patentability," for PCT Application No. PCT/US2016/024614 mailed Oct. 19, 2017 (7 pages).
"International Preliminary Report on Patentability," for PCT Application No. PCT/US2016/024753 mailed Oct. 19, 2017 (7 pages).
"International Preliminary Report on Patentability," for PCT Application No. PCT/US2016/039808 mailed Jan. 11, 2018 (8 pages).
"International Preliminary Report on Patentability," for PCT Application No. PCT/US2016/041757 mailed Jan. 25, 2018 (8 pages).
"International Preliminary Report on Patentability," for PCT Application No. PCT/US2016/050691 mailed Mar. 29, 2018 (9 pages).

(56) References Cited

OTHER PUBLICATIONS

"International Preliminary Report on Patentability," for PCT Application No. PCT/US2017/032656 mailed Nov. 29, 2018 (7 pages).
"International Preliminary Report on Patentability," for PCT Application No. PCT/US2018/028864 mailed Nov. 7, 2019 (7 pages).
"International Search Report & Written Opinion," for International Application No. PCT/US2013/048976, mailed Nov. 19, 2013 (20 pages).
"International Search Report and Written Opinion," for PCT Application No. PCT/US2016/041757 mailed Oct. 12, 2016 (12 pages).
"International Search Report and Written Opinion," for PCT application No. PCT/US2016/050691 mailed Dec. 19, 2016 (14 pages).
"International Search Report and Written Opinion," for PCT Application No. PCT/US2017/032656 mailed Jul. 21, 2017 (16 pages).
"International Search Report and Written Opinion," for PCT Application No. PCT/US2018/028864 mailed Jul. 30, 2018 (10 pages).
"International Search Report and Written Opinion," for PCT/US2016/024614 mailed Jul. 12, 2016 (13 pages).
"International Search Report and Written Opinion," for PCT/US2016/024753 mailed Jul. 22, 2016 (11 pages).
"International Search Report and Written Opinion," for PCT/US2016/039808 mailed Sep. 26, 2016 (11 pages).
Jen, Shih-Hui et al., "Critical tensile and compressive strains for cracking of al2O3 films grown by atomic layer deposition," Journal of Applied Physics 109, 084305 (2011), 11 pages.
Jen, Shih-Hui et al., "Critical tensile strain and water vapor transmission rate for nanolaminate films grown using al2o3 atomic layer deposition and alucone molecular layer deposition," Applied Physics Letters 101, 234103 (2012), 3 pages.
Jiang, Shaoyi et al., "Ultralow-Fouling, Functionalizable, and Hydrolyzable Zwitterionic Materials and Their Derivatives for Biological Applications," Adv Mater. Mar. 5, 2010;22(9):920-32 (13 pages).
Kalejs, et al., "St. Jude Epic Heart Valve Bioprostheses Versus Native Human and Porcine Aortic Valves—Comparison of Mechanical Properties," Interactive Cardiovascular and Thoracic Surgery 8 (2009) 553-557.
Kalfon-Cohen, Estelle et al., "Microstructure and nematic transition in thermotropic liquid crystalline fibers and their single polymer composites," Polym. Adv. Technol., 2007. 18(9): p. 771-779 (9 pages).
Kang, Jungmee et al., "Polyisobutylene-Based Polyurethanes with Unprecedented Properties and How They Came About," Journal of Polymer Science Part A: Polymer Chemistry, 2011. 49(18): p. 3891-3904 (14 pages).
Khondker, O.A. et al., "Fabrication and mechanical properties of aramid/nylon plain knitted composites," Composites Part A: Applied Science and Manufacturing, 2004. 35(10): p. 1195-1205 (11 pages).
Kim, Nam K. et al., "Nanofibrillar Poly(vinylidene fluoride): Preparation and Functional Properties," Int. J. Polym. Mater. Polym. Biomater., 2014. 63(1): p. 23-32 (10 pages).
Kim, Nam K. et al., "Polymer-Polymer and Single Polymer Composites Involving Nanofibrillar Poly(vinylidene Fluoride): Manufacturing and Mechanical Properties," J. Macromol. Sci., Part B: Phys., 2014. 53(7): p. 1168-1181 (14 pages).
Kuang, Jinghao et al., "Universal Surface-initiated Polymerization of Antifouling Zwitterionic Brushes Using a Mussel Mimetic Peptide Initiator," Langmuir. May 8, 2012; 28(18): 7258-7266 (20 pages).
Lane, Bobby "What Line Should I Use?," Bassmaster.com (www.bassmaster.com/tips/ask-experts-what-line-should-i-use) Apr. 2013, 1-7.
"Liquid-Crystal Polymer," Wikipedia, the Free Encyclopedia <http://en/wikipedia.org/wiki/Liquid-crystal_polymer>, retrieved Jun. 2, 2016 (3 pages).
Liu, et al., "Effect of fiber orientation on the stress distribution within a leaflet of a polymer composite heart valve in the closed position," J of Biomedichanics, 2007, 40:1099-1106 (8 pages).
Mach, H. et al., "Highly Reactive Polyisobutene as a Component of a New Generation of Lubricant and Fuel Additives," Lubrication Science 1999, 11 (2), 175-185 (11 pages).

Madhusha, "Difference between Fluorine and Fluoride," Aug. 9, 2017, PEDIAA.com, pp. 1-8. URL <http://pediaa.com/difference-between-fluorine-and-fluoride/> (8 pages).
Maity, J. et al., "Homocomposites of chopped fluorinated polyethylene fiber with low-density polyethylene matrix," Mater. Sci. Eng., A, 2008. A479(1-2): p. 125-135 (11 pages).
Masoumi, et al., "Trilayered Elastomeric Scaffolds for Engineering Heart Valve Leaflets," Biomaterials. Sep. 2014; 35(27):7774-7785.
Matabola, K. P. et al., "Single polymer composites: a review," Journal of Materials Science, 2009. 44(23): p. 6213-6222 (10 pages).
McKenna, H. A. et al., "Handbook of Fibre Rope Technology," The Textile Institute, Woodhead Publishing Limited, Cambridge England 2004, 1-432.
Medeiros Araujo, Thiago et al., "Liquid crystalline single-polymer short-fibers composites," Composite Interfaces, 2013. 20(4): p. 287-298 (12 pages).
Mitchell, J. "Braided Fishing Lines (Superlines)," Sufix Fishing Lines Product page as it appeared Apr. 5, 2019 (https://sufix.fishing/braided-fishing-lines-superlines), 1-5.
"Notification of Patent Reexamination," for Chinese Patent Application No. 201380044842.0 mailed Feb. 7, 2018 (12 pages) with English summary.
"Office Action," for Japanese Patent Application No. 2017-549776 mailed Dec. 17, 2019 (9 pages) with English Translation.
"Office Action," for Japanese Patent Application No. 2017-549776 mailed Jun. 2, 2020 (4 pages) with English Summary.
"Office Action," for Japanese Patent Application No. 2017552443 mailed Dec. 17, 2019 (14 pages) with English Translation.
"Office Action," for Japanese Patent Application No. 2017-552443 mailed Sep. 15, 2020 (10 pages) with English Translation.
"Office Action," for Japanese Patent Application No. 2017-564627 mailed Jan. 21, 2020 (9 pages) with English Translation.
"Office Action," for Japanese Patent Application No. 2018-501287 mailed Dec. 1, 2020 (9 pages) with English Translation.
"Office Action," for Japanese Patent Application No. 2018513335 mailed Aug. 4, 2020 (5 pages) with English Translation.
"Office Action," for Japanese Patent Application No. 2019-557835 mailed Sep. 8, 2020 (6 pages) with English Translation.
"Office Action," for JP Patent Application No. 2018-501287 mailed Jun. 2, 2020 (6 pages) with English Summary.
Ohri, Rachit et al., "Hyaluronic acid grafting mitigates calcification of glutaraldehyde-fixed bovine pericardium," J Biomed Mater Res 70A: 328-334, 2004 (7 pages).
Raghavan, R. et al., "Nanocrystalline-to-amorphous transition in nanolaminates grown by low temperature atomic layer deposition and related mechanical properties," Applied Physics Letters 100, 191912 (2012), 9 pages.
"Response to First Examination Report," for Australian Patent Application No. 2016285561 filed May 18, 2020 (11 pages).
Rutledge, G.C. et al., "Electrostatic Spinning and Properties of Ultrafine Fibers," National Textile Center Annual Report: Nov. 2001, M01-D22, (10 pages).
Schneider, Tobias et al., "Influence of fiber orientation in electrospun polymer scaffolds on viability, adhesion and differentiation of articular chondrocytes," Clinical Hemorheology and Microcirculation 52 (2012) 325-336 (13 pages).
"Second Office Action," for Chinese Patent Application No. 201380044842.0, mailed Aug. 12, 2016 (16 pages) with summary.
"Second Office Action," for Chinese Patent Application No. 201680018663.3 mailed Dec. 16, 2020 (6 pages) with English Summary.
"Second Office Action," for Chinese Patent Application No. 201680018700.0 mailed Jul. 12, 2019 (11 pages) with English Summary.
"Second Office Action," for Chinese Patent Application No. 201680036250.8 mailed Jul. 11, 2019 (7 pages) with English Summary.
"Second Office Action," for Chinese Patent Application No. 201680040898.2 mailed Nov. 4, 2019 (12 pages), with English Summary.

(56) References Cited

OTHER PUBLICATIONS

Shin, Y. M. et al., "Experimental characterization of electrospinning: the electrically forced jet and instabilities," Polymer 42 (2001) 9955-9967 (13 pages).
Sun, Xiaoli et al., "α and β Interfacial Structures of the iPP/PET Matrix/Fiber Systems," Macromolecules, 2007. 40(23): p. 8244-8249 (6 pages).
Szeghalmi, Adriana et al., "All dielectric hard x-ray mirror by atomic layer deposition," Applied Physics Letters 94, 133111 (2009), 3 pages.
Szilagyi, Imre M. et al., "Review on One-Dimensional Nanostructures Prepared by Electrospinning and Atomic Layer Deposition," INERA Workshop of ISCMP2014, IOP Publishing, Journal of Physics: Conference Series 559, 2014 (13 pages).
"Third Office Action," for Chinese Patent Application No., 201680036250.8 mailed Mar. 2, 2020 (10 pages) with English Summary.
"Third Office Action," for Chinese Patent Application No. 201380044842.0 mailed Dec. 29, 2018 (12 pages), with English translation.
"Third Office Action," for Chinese Patent Application No. 201680018700.0 mailed Feb. 3, 2020 (8 pages) with English Summary.
Tu, Qin et al., "Synthesis of polyethylene glycol- and sulfobetaine-conjugated zwitterionic poly(I-lactide) and assay of its antifouling properties," Colloids and Surfaces B; Biointerfaces 102 (2013) 331-340 (10 pages).
Vesely, et al., "Micromechanics of the Fibrosa and the Ventricularis in Aortic Valve Leaflets," J Biomech. 1992 25(1):101-113.
Vick, Linda W. et al., "Hot compaction and consolidation of polycarbonate powder," Polym. Eng. Sci., 1998. 38(11): p. 1824-1837 (14 pages).
Wang, Qiang et al., "A novel small animal model for biocompatibility assessment of polymeric materials for use in prosthetic heart valves," J Biomed Mater Res 93A: 442-453, 2010 (12 pages).
Wang, Qiang et al., "In-Vivo Assessment of a Novel Polymer (SIBS) Trileaflet Heart Valve," J Heart Valve Dis, Jul. 2010, 19(4):499-505 (7 pages).
Ward, I.M. et al., "Developments in oriented polymers," Plastics, Rubber and Composites, 2004. 33(5): p. 189-194 (6 pages).
Ward, I.M. et al., "Novel composites by hot compaction of fibers," Polym. Eng. Sci., 1997. 37(11): p. 1809-1814 (6 pages).
Wheatley, et al., "Polyurethane: material for the next generation of heart valve prostheses?," Eur J Cardio-Thoracic Surg, 2000, 17:440-448 (11 pages).
"Why Use Superlines?," Berkley-Fishing.com (www.berkley-fishing.com/Berkley-ae-why-use-superlines.html), 1-6.
Yang, Mingjing et al., "Assessing the Resistance to Calcification of Polyurethane Membranes Used in the Manufacture of Ventricles for a Totally Implantable Artificial Heart," J Biomed Mater Res (Appl Biomater) 48: 648-659, 1999 (12 pages).
Yao, Jian et al., "High Strength and High Modulus Electrospun Nanofibers," Fibers 2014; 2:158-187 (30 pages).
Yeh, Shiou-Bang et al., "Modification of Silicone Elastomer with Zwitterionic Silane for Durable Antifouling Properties," Langmuir 2014, 30, 11386-11393 (8 pages).
Zhang, Baoyan et al., "Studies of Novel Segmented Copolyether Polyurethanes," Eur. Polym. J., vol. 34, No. 3-4, pp. 571-575 (1998) (5 pages).
Zhang, Zhiping et al., "Effect of Crosslinking and Grafting by 60Co-γ-ray Irradiation on Carbon Black/Polyethylene Switching Materials and Fluoride Resin System in self-regulating Heating Cables," JAERI-Conf, 2000. 2000-001(JCBSRC '99, the 8th Japan-China Bilateral Symposium on Radiation Chemistry, 1999): p. 202-210 (9 pages).
Zhao, Zeng Hua et al., "Research development of single polymer composite preparation," Gongcheng Suliao Yingyong, 2010. 38(2): p. 81-84, with machine translation (11 pages).
"Communication Pursuant to Article 94(3) EPC," for European Patent Application No. 18723271.5 mailed Feb. 16, 2022 (6 pages).
"Non-Final Office Action," for U.S. Appl. No. 16/526,150 mailed Mar. 9, 2022 (61 pages).
"Rejection Decision," for Chinese patent application No. 201880024683.0 mailed Apr. 15, 2022 (8 pages) with English Summary.
"Response to Communication Pursuant to Article 94(3) EPC," for European Patent Application No. 18723271.5 filed Jun. 23, 2022 (11 pages).
"Response to Non-Final Rejection," mailed on Mar. 9, 2022 for U.S. Appl. No. 16/526,150, submitted via EFS-Web on Jun. 9, 2022, 8 pages.
"Notification of Reexamination," for Chinese Patent Application No. 201380044842.0 mailed Sep. 26, 2021 (21 pages) with English translation.
"Response to Non-Final Rejection," mailed on Jul. 20, 2021 for U.S. Appl. No. 16/413,104, submitted via EFS-Web on Oct. 19, 2021, 12 pages.
"First Office Action," for Chinese Patent Application No. 201880024683.0 mailed May 28, 2021 (11 pages) with English Summary.
"Non-Final Office Action," for U.S. Appl. No. 16/413,104 mailed Jul. 20, 2021 (74 pages).
"Office Action," for Japanese Patent Application No. 2018-501287 mailed Jun. 15, 2021 (4 pages).
"Response to Communication Pursuant to Article 94(3) EPC," for European Patent Application No. 16715724.7 filed Aug. 9, 2021 (53 pages).
"Response to Communication Pursuant to Rules 161(1) and 162 EPC," for European Patent Application No. 20815764.4 filed Jan. 17, 2023 (11 pages).
"Office Action," for Japanese Patent Application No. 2022-529907 mailed Apr. 18, 2023 (12 pages) with English translation.
"Communication Pursuant to Article 94(3) EPC," for European Patent Application No. 18723271.5 mailed Mar. 18, 2024 (6 pages).
"Decision of Rejection," for Japanese Patent Application No. 2022-529907 mailed Oct. 31, 2023 (10 pages) with English Translation.
"Non-Final Office Action," for U.S. Appl. No. 17/179,971 mailed Feb. 22, 2024 (63 pages).
"First Office Action," for Chinese Patent Application No. 202080081205.0 mailed Aug. 30, 2024 (13 pages) with English Summary.

\* cited by examiner

COMPOSITE WEB-POLYMER HEART VALVE

This application claims the benefit of U.S. Provisional Application No. 62/940,681 filed Nov. 26, 2019, the content of which is herein incorporated by reference in its entirety.

FIELD

Embodiments herein relate to prosthetic heart valves. More specifically, embodiments herein relate to polymer coated prosthetic heart valves.

BACKGROUND

Heart function can be significantly impaired when a heart valve is not functioning properly. Potential causes for heart valve malfunction include dilation of an annulus around the valve, ventricular dilation, a prolapsed or misshapen valve leaflet, and stenosis, such as aortic stenosis. When the heart valve is unable to close properly, the blood within a heart chamber can regurgitate, or leak backwards through the valve. When the heart valve is unable to open properly, forward blood flow (e.g. systolic blood flow) can be impaired.

Valve malfunction may be treated by replacing or repairing a diseased valve, such as an aortic valve. Surgical valve replacement is one method for treating the diseased valve. Minimally invasive methods of treatment, such as transcatheter aortic valve replacement (TAVR), generally involve the use of delivery catheters that are delivered through arterial passageways or other anatomical routes into the heart to replace the diseased valve with an implantable prosthetic heart valve. Leaflets of such valves have been formed from various materials including synthetic materials and animal tissues.

SUMMARY

Embodiments herein relate to polymer coated prosthetic heart valves. In a first aspect, a method of manufacturing a heart valve is included, the method including obtaining a frame, attaching a porous web to the frame, and applying a coating over at least a portion of the porous web.

In a second aspect, in addition to one or more of the preceding or following aspects, or in the alternative to some aspects, the porous web includes a mesh.

In a third aspect, in addition to one or more of the preceding or following aspects, or in the alternative to some aspects, at least a portion of the porous web that is coated corresponds to a leaflet of the heart valve.

In a fourth aspect, in addition to one or more of the preceding or following aspects, or in the alternative to some aspects, the porous web can include a polymeric web.

In a fifth aspect, in addition to one or more of the preceding or following aspects, or in the alternative to some aspects, the coating can include a polymeric coating.

In a sixth aspect, in addition to one or more of the preceding or following aspects, or in the alternative to some aspects, attaching the porous web to the frame includes suturing the porous web to the frame.

In a seventh aspect, in addition to one or more of the preceding or following aspects, or in the alternative to some aspects, applying the coating over the porous web includes coating a plurality of sutures attaching the porous web to the frame.

In an eighth aspect, in addition to one or more of the preceding or following aspects, or in the alternative to some aspects, applying a coating over the porous web occludes pores within the porous web.

In a ninth aspect, in addition to one or more of the preceding or following aspects, or in the alternative to some aspects, the porous web defines at least one valve leaflet.

In a tenth aspect, in addition to one or more of the preceding or following aspects, or in the alternative to some aspects, the method further can include attaching an electrospun substrate to at least one of the frame and the porous web.

In an eleventh aspect, in addition to one or more of the preceding or following aspects, or in the alternative to some aspects, the electrospun substrate corresponds to at least one valve leaflet.

In a twelfth aspect, in addition to one or more of the preceding or following aspects, or in the alternative to some aspects, the electrospun substrate includes a polyisobutylene urethane (PIB-PUR) copolymer.

In a thirteenth aspect, in addition to one or more of the preceding or following aspects, or in the alternative to some aspects, the porous web includes polyethylene terephthalate.

In a fourteenth aspect, in addition to one or more of the preceding or following aspects, or in the alternative to some aspects, applying a coating over the porous web includes dip coating the coating onto the porous web.

In a fifteenth aspect, a method of manufacturing a heart valve is included, the method including obtaining a frame, attaching a porous web to the frame, applying a coating over the porous web, attaching an electrospun fiber mat to the frame, and applying a coating over the electrospun fiber mat.

In a sixteenth aspect, a heart valve is included. The heart valve including a frame, a plurality of valve leaflets attached to the frame, and wherein each valve leaflet has a first polymer forming a porous support web, and a second polymer forming a coating occluding pores in the porous support web, wherein the valve leaflets are attached to the frame with a connection structure that is at least partially covered by the coating.

In a seventeenth aspect, in addition to one or more of the preceding or following aspects, or in the alternative to some aspects, the connection structure can include a plurality of sutures.

In an eighteenth aspect, in addition to one or more of the preceding or following aspects, or in the alternative to some aspects, wherein the plurality of sutures is covered with the second polymer.

In a nineteenth aspect, in addition to one or more of the preceding or following aspects, or in the alternative to some aspects, the valve can include an inner skirt, wherein the inner skirt includes the first polymer forming a porous support web, and the second polymer forming a coating occluding pores in the porous support web, wherein the inner skirt is attached to the frame with a connection structure that does not pass through the coating.

In a twentieth aspect, in addition to one or more of the preceding or following aspects, or in the alternative to some aspects, the connection structure can include a plurality of sutures.

In a twenty-first aspect, in addition to one or more of the preceding or following aspects, or in the alternative to some aspects, the valve can further include an outer sealing skirt.

In a twenty-second aspect, in addition to one or more of the preceding or following aspects, or in the alternative to some aspects, wherein the outer sealing skirt includes the first polymer forming a porous support web, and the second polymer forming a coating occluding pores in the porous support web, wherein the outer sealing skirt is attached to the frame with a connection structure that does not pass through the coating.

In a twenty-third aspect, in addition to one or more of the preceding or following aspects, or in the alternative to some aspects, the connection structure can include a plurality of sutures.

In a twenty-fourth aspect, in addition to one or more of the preceding or following aspects, or in the alternative to some aspects, wherein the frame is configured to be collapsible for transcatheter delivery and expandable for implantation at an implantation site.

In a twenty-fifth aspect, a heart valve is included having a frame, a porous web defining structural features of the valve, an attachment structure securing the porous web to the frame, and a polymeric coating disposed over the porous web and the attachment structure and occluding pores in the porous web.

In a twenty-sixth aspect, in addition to one or more of the preceding or following aspects, or in the alternative to some aspects, the structural features of the valve can include at least one of a valve leaflet, an inner skirt, and an outer sealing skirt.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

In some cases, prosthetic heart valves can be formed with synthetic materials attached to a frame, wherein the synthetic materials are fully formed first and then sutured onto the frame. However, in such a scenario the sutures penetrate through the full thickness of the synthetic materials, forming points of lesser structural integrity.

In accordance with various embodiments herein, prosthetic heart valves can be formed through a process wherein a portion of a synthetic valve material (such as a support web or mesh) is first attached to a frame (using sutures or other attachment elements) and thereafter coated or otherwise permeated with a polymeric material. In this manner, the sutures or other attachment elements do not penetrate through the polymeric coating allowing for more robust structural integrity.

As such, in various embodiments, a heart valve is included having a frame and a plurality of valve leaflets attached to the frame. Each valve leaflet can include a first polymer forming a porous support web and a second polymer forming a coating occluding pores in the porous support web. The valve leaflets can be attached to the frame with a connection structure that is at least partially covered by the coating (versus the connection structure penetrating through the coating). Further, various embodiments herein include a coating process to develop portions of the prosthetic heart valve, such as the leaflets, an inner skirt, and/or an outer skirt.

Figure 1:
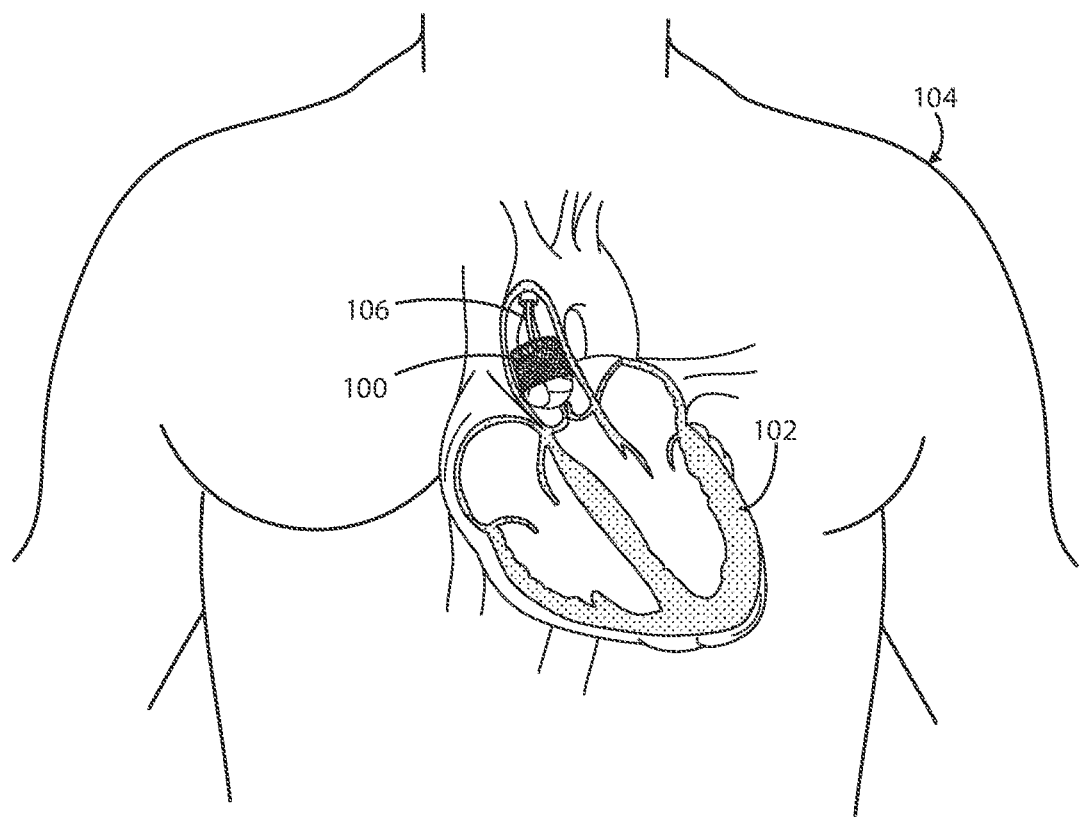
FIG. 1 is a schematic view of a prosthetic heart valve within a human body in accordance with various embodiments herein.

Referring now to FIG. 1, a schematic view of a prosthetic heart valve 100 within a heart 102 of a human body 104 is shown in accordance with various embodiments herein. The heart has four heart valves: a pulmonary valve, a tricuspid valve, an aortic valve and a mitral valve. The heart valves allow blood to pass through the heart and into major blood vessels connected to the heart, for example, the aorta and pulmonary artery. Prosthetic heart valve 100 of FIG. 1 can be surgically implanted or delivered through blood vessels using a delivery device or catheter 106. The delivery catheter 106 can be inserted into a femoral, subclavian, transapical, transseptal, transatrial, or an aortic incision during a transcatheter aortic valve replacement (TAVR) procedure or during implantation of a mitral valve. In various embodiments, the delivery catheter 106 can include a transfemoral delivery catheter 106. Once inserted, the delivery catheter 106 can deliver the prosthetic heart valve 100 to the desired location within the anatomy and release the heart valve 100 at a desired implantation site. Although FIG. 1 shows prosthetic heart valve 100 replacing an aortic valve, in some cases, prosthetic heart valve 100 can be a replacement for another type of heart valve (e.g., a mitral valve or a tricuspid valve). In some examples the heart valve is specifically a TAVI (transcatheter aortic valve implantation) valve.

Figure 2:
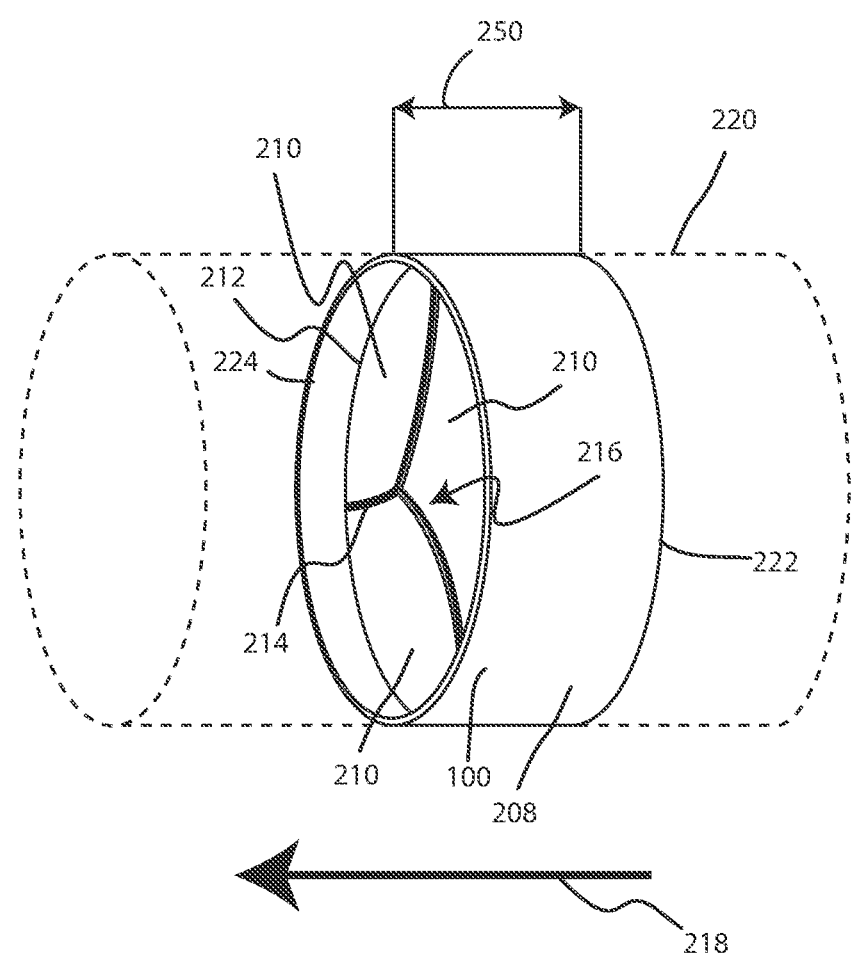
FIG. 2 is a schematic view of a prosthetic heart valve in a vessel in accordance with various embodiments herein.
Figure 3:
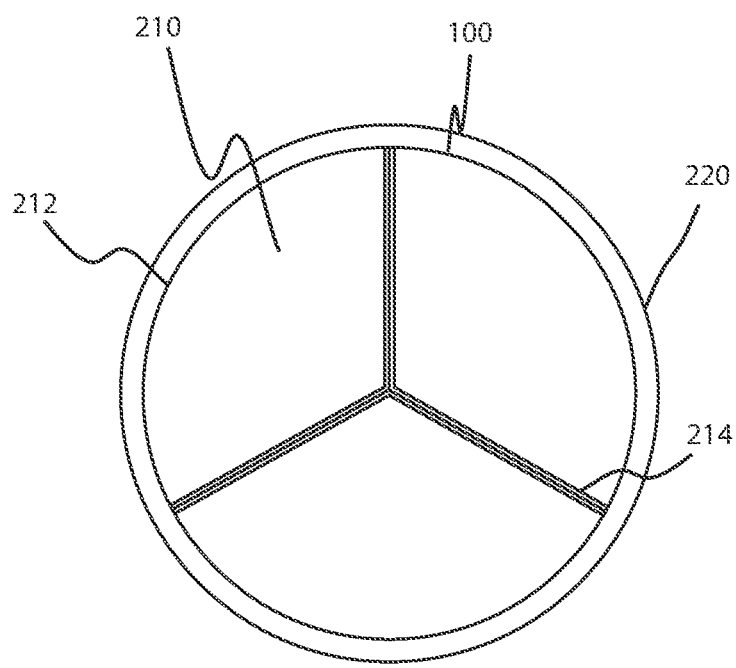
FIG. 3 is an end view of a prosthetic heart valve in accordance with various embodiments herein.

FIG. 2 shows a schematic view of a closed heart valve 100 in a vessel 220, according to various embodiments. FIG. 3 shows an end view of the closed heart valve 100. The valve 100 can be configured to allow one-way flow through the valve 100, such as depicted by arrow 218. In an embodiment, the arrow 218 represents blood flow during systole. The heart valve 100 can include an inlet 222 and an outlet 224.

In various embodiments, the heart valve 100 includes a frame 208. The frame 208 can define a central lumen which, in some embodiments, can be substantially cylindrical. The side of the frame 208 and other components facing the central lumen can be referred to as the luminal surface or luminal side. The opposite side of the frame 208 and other components (e.g., facing away from the central lumen) can be referred to as the abluminal surface or abluminal side. In various embodiments, the frame 208 can have a substantially circular cross-section. In other embodiments, the frame 208 can have a non-circular, such as a D-shaped, cross-section. In some embodiments, a non-circular frame 208 can be used to repair a mitral valve or another non-circular valve in the body. Various specific frame designs and geometries can be used. Frames can be manufactured using various techniques including, but not limited to, machining, laser-cutting, sintering, direct metal laser sintering (DMLS), casting, cutting, drilling, molding, welding, stamping, tempering, extrusion, and the like.

The heart valve 100 can also include a plurality of valve leaflets 210, such as two or three leaflets 210. The heart valve 100 can include a coaptation region 216, such as where one or more leaflets 210 meet to close the valve 100 or separate to open the valve 100. In various embodiments, the valve leaflets 210 are coupled directly or indirectly to the frame 208, e.g. for support by the frame 208. The valve leaflets 210 can include a root edge 212, such as an edge of the leaflet 210 that is coupled to or adjacent to the frame 208. The valve leaflets 210 can also include a coaptation edge 214, such as an edge that aligns with an edge of an adjacent valve leaflet 210. The coaptation edge 214 can be movable relative to the root edge 212 to coapt with the coaptation edges 214 of the other leaflets 210. The coaptation edges 214 of the leaflets 210 move into coaptation with one another in a closed position (FIGS. 2 and 3) to substantially restrict fluid from flowing past the valve 100 in a direction opposite to arrow 218. Specifically, the leaflets 210 can coapt to fill up or close the central lumen of the valve 100 thereby impeding the flow of fluid opposite to arrow 218.

The heart valve 100 can have a longitudinal length 250. The longitudinal length 250 can have a length of various dimensions. In some embodiments, the length can be greater than or equal to 20 mm, 22 mm, 24 mm, 26 mm, 28 mm, 30 mm, 32 mm, 35 mm, 38 mm, 40 mm, 42 mm, 45 mm, 48 mm, or 50 mm. In some embodiments, the length 250 can be less than or equal to 70 mm, 68 mm, 65 mm, 62 mm, 60 mm, 58 mm, 55 mm, 52 mm, or 50 mm. In some embodiments, the length can fall within a range of 20 mm to 70 mm, or 24 mm to 68 mm, or 30 mm to 65 mm, or 35 mm to 62 mm, or 40 mm to 60 mm, or 42 mm to 58 mm, or 45 mm to 55 mm, or 48 mm to 52 mm, or can be about 50 mm.

In various embodiments, the inner diameter of the central lumen can be at least 10 mm and not more than 50 mm. In various embodiments, the inner diameter of the central lumen can be at least 15 mm and not more than 40 mm. In various embodiments, the inner diameter of the central lumen can be at least 20 mm and not more than 35 mm.

Figure 4:
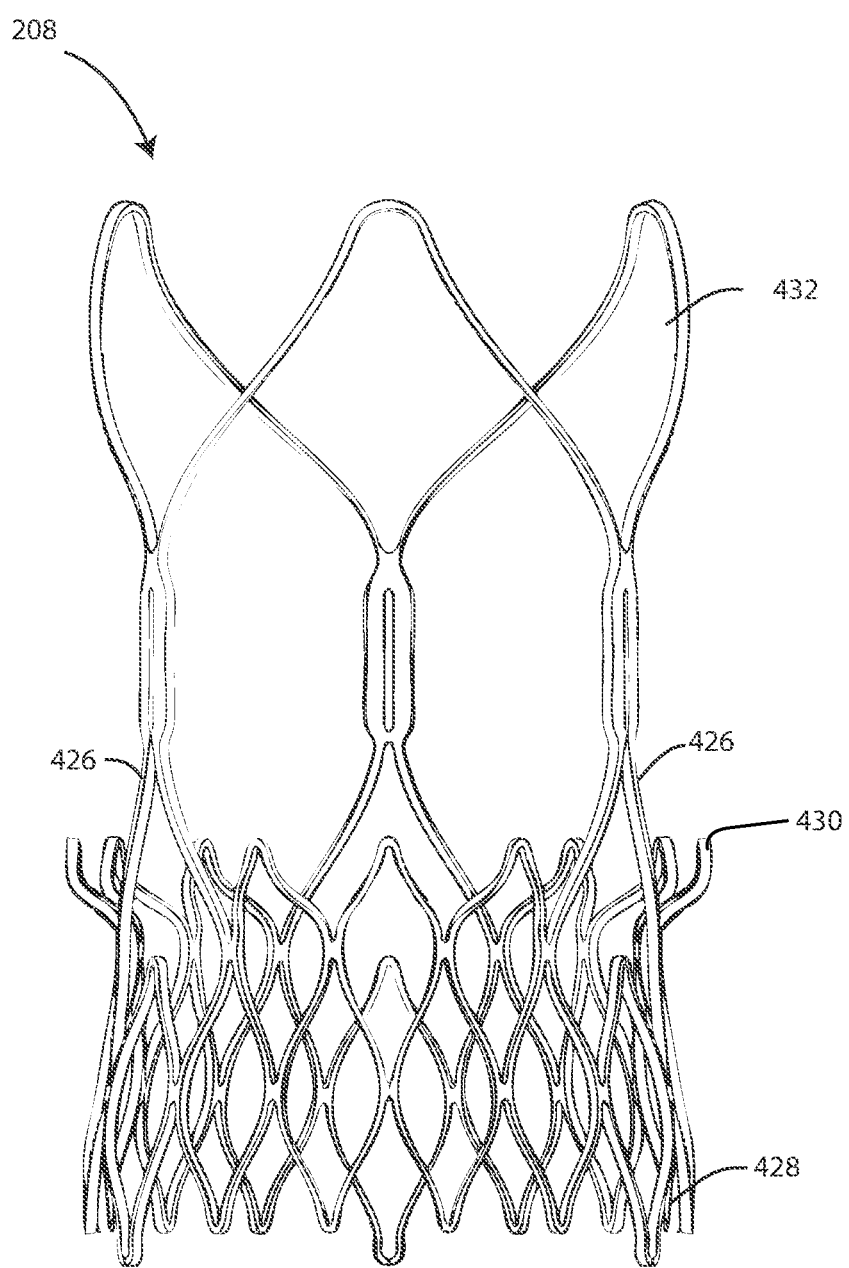
FIG. 4 is a view of a frame in accordance with various embodiments herein.

Referring now to FIG. 4, a view of a frame 208 is shown in accordance with various embodiments herein. A heart valve 100 can include a frame 208. The frame 208 includes a plurality of struts 426. The frame 208 can also include a lower crown 428, an upper crown 430, and one or more stabilization arches 432. In various embodiments, the frame 208 can be configured to be collapsible for transcatheter delivery and expandable for implantation at an implantation site. The frame 208 can be formed of various materials including, but not limited to, metals (elemental or alloys), polymers, composites, and the like. In some embodiments, the frame 208 can specifically include nitinol, NiTi, titanium, stainless steel, 316L, L605, MP35N, or the like.

Figure 5:
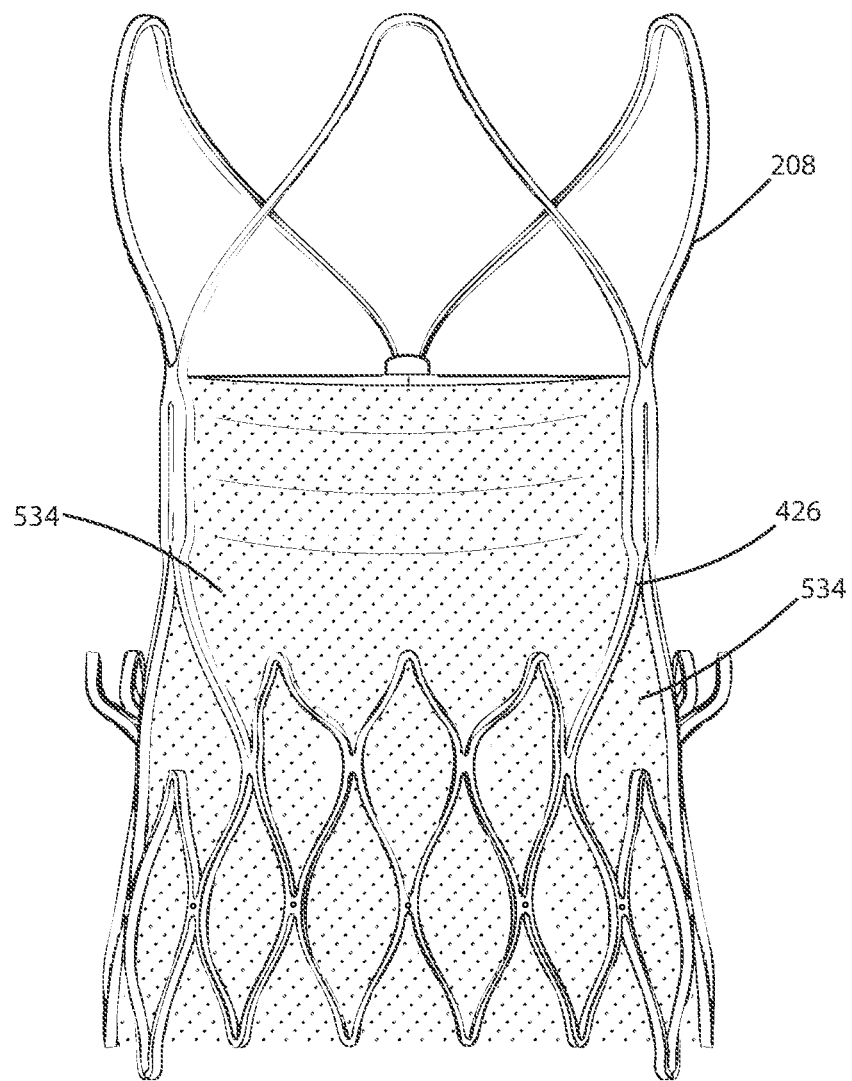
FIG. 5 is a front view of a frame and a web in accordance with various embodiments herein.

Referring now to FIG. 5, a front view of a heart valve 100 including a frame 208 and a web 534 is shown in accordance with various embodiments herein. Detailed aspects of exemplary webs are provided in greater detail below. The web 534 can provide a support structure or scaffolding for portions of the heart valve 100. The web 534 can provide a support structure or scaffolding onto which a polymer is applied in order to form portions of the heart valve 100. In various embodiments, the web 534 defines at least one valve leaflet. In various embodiments, the web 534 can be porous, such as having openings through which a coating can pass through during a coating process, such as to coat the luminal side and the abluminal sides of the valve 100. The coating can also occlude the pores in the web 534, such as to prevent blood from flowing through the valve 100 in unintended directions after implantation into a patient.

The pores can be of various sizes, depending on the nature of the web used. By way of example, the pores can have a mean pore size (major axis) of about 0.01, 0.02, 0.03, 0.04, 0.05, 0.075, 0.1, 0.125, 0.15, 0.175, 0.2, 0.25, 0.3, 0.35, 0.4, 0.5, 0.6, 0.7, 0.8, 0.9, 1, 1.1, 1.2, 1.3, 1.4, 1.5, 1.75, 2, 2.5, 3, 4, 5, 6, 7, or 8 mm, or an amount falling within a range between any of the foregoing.

Figure 6:
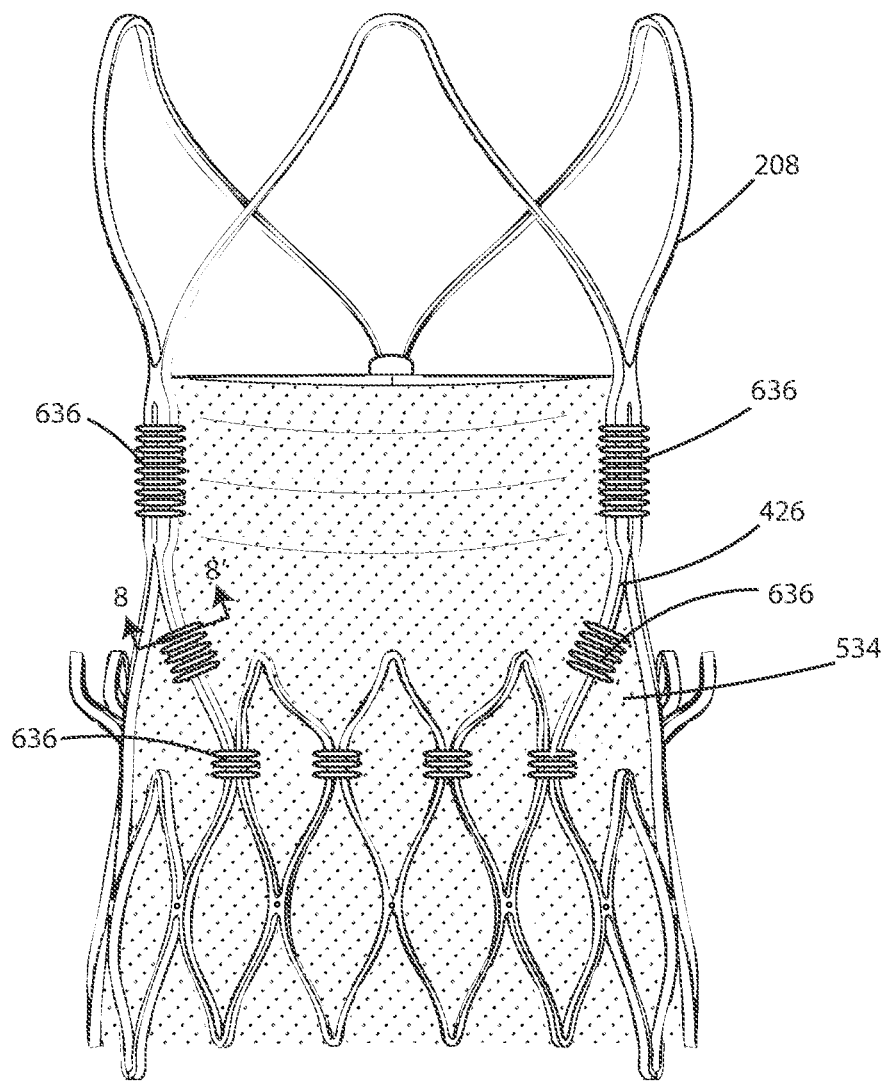
FIG. 6 is a front view of a frame and a web in accordance with various embodiments herein.

FIG. 5 shows the web 534 aligned with the frame 208. The web 534 can be aligned with the frame 208 prior to attaching or coupling the web 534 to the frame 208. In various embodiments, the web 534 can be attached or coupled to the frame 208 with an attachment structure. Referring now to FIG. 6, a front view of a frame 208 with a web 534 sutured to the frame 208 is shown in accordance with various embodiments herein. In some embodiments, the attachment structure that attaches the web 534 to the frame 208 can include a plurality of sutures 636. The illustrated sutures 636 shown in FIG. 6 can be suitable for supporting a leaflet portion of the web with respect to the frame 208. More sutures 636 or fewer sutures 636 can be used as appropriate. Additional sutures 636 can be provided to attach the web to the frame 208 at other positions, for example, at one or more lower regions of the frame 208 and/or the lower crown. In various embodiments, attaching the web 534 to the frame 208 can include suturing the web 534 to the frame 208 such as with a plurality of sutures 636. Other attachment structures can include staples, clamps, loops, bands, or the like.

Figure 7:
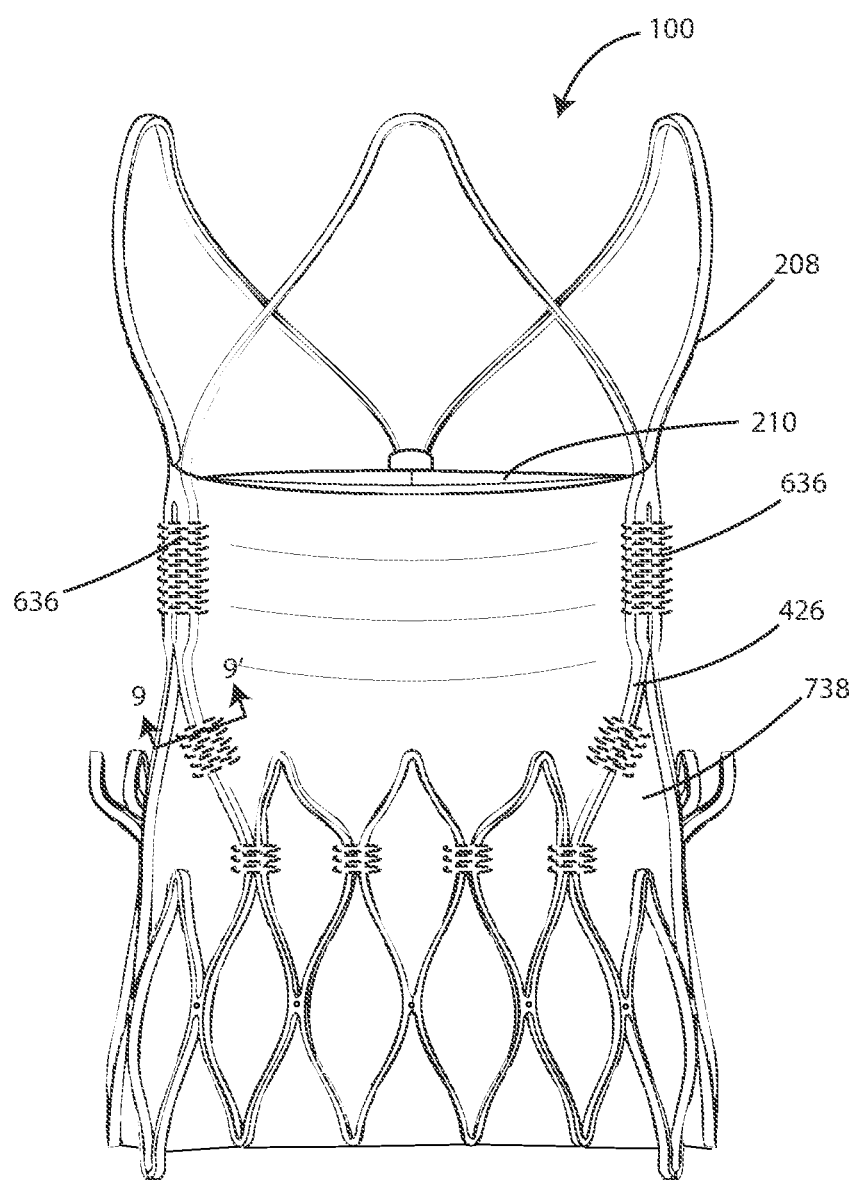
FIG. 7 is a front view of a prosthetic heart valve in accordance with various embodiments herein.

The uncoated frame 208, web 534, and sutures 636 as shown in FIG. 6 can be coated with a coating to result in the heart valve 100 shown in FIG. 7. FIG. 7 shows a front view of a prosthetic heart valve 100 in accordance with various embodiments herein. The heart valve 100 includes a frame 208, a plurality of valve leaflets 210, and a plurality of sutures 636 attaching the web to the frame 208. The heart valve 100 can further include a coating 738, such as a polymeric coating. Exemplary coatings are described below in the section on applied coating materials.

In various embodiments, a heart valve 100 can include a frame 208 and a plurality of valve leaflets 210 attached to the frame 208. In various embodiments, each valve leaflet 210 can include a first polymer forming a support web 534, and a second polymer forming a coating occluding pores (described further below) in the porous support web 534. The valve leaflets 210 can be attached to the frame 208 with a connection structure, such as sutures, that can be at least partially covered by the coating 738.

In various embodiments, the connection structure can include a plurality of sutures 636. In various embodiments, a heart valve 100 can include a frame 208, a porous web 534 that can define structural features (leaflets, inner skirt, outer skirt, etc.) of the valve 100, an attachment structure securing the porous web 534 to the frame 208, and a polymeric coating 738. The coating 738 can be disposed over the porous web 534, the attachment structure, and the frame 208. The coating can occlude pores in the porous web 534.

In some embodiments, the coating 738 can be applied to the web 534 after the web 534 has been attached to the frame 208. In some embodiments, the coating 738 can be applied to the heart valve 100 by a dip coating process, such as submerging the frame 208, the web 534, and the sutures 636 into a supply of coating 738, such as a liquid coating that solidifies on the heart valve 100. In some embodiments, the coating 738 can be applied to the heart valve 100 by a spray coating process, such as by spraying the frame 208, the web 534, and the sutures 636 with the coating 738. In some embodiments, the entire frame 208 and web 534 can be sprayed. However, in other embodiments, one or more masks can be used to cover portions of the frame 208 and/or web 534, such that only certain portions are spray coated. For example, in some embodiments, stabilization arches can be masked such that they are not coated by the applied polymer whereas other portions of the valve are coated.

In various embodiments, the coating 738 can be disposed over the porous web 534 and the attachment structure resulting in occluding pores in the porous web 534. In various embodiments, at least a portion of the porous web 534 that is coated corresponds to a leaflet 210 of the heart valve 100. In various embodiments, the valve leaflets 210 each include a portion of the web 534 and a portion of the coating 738.

Figure 8:
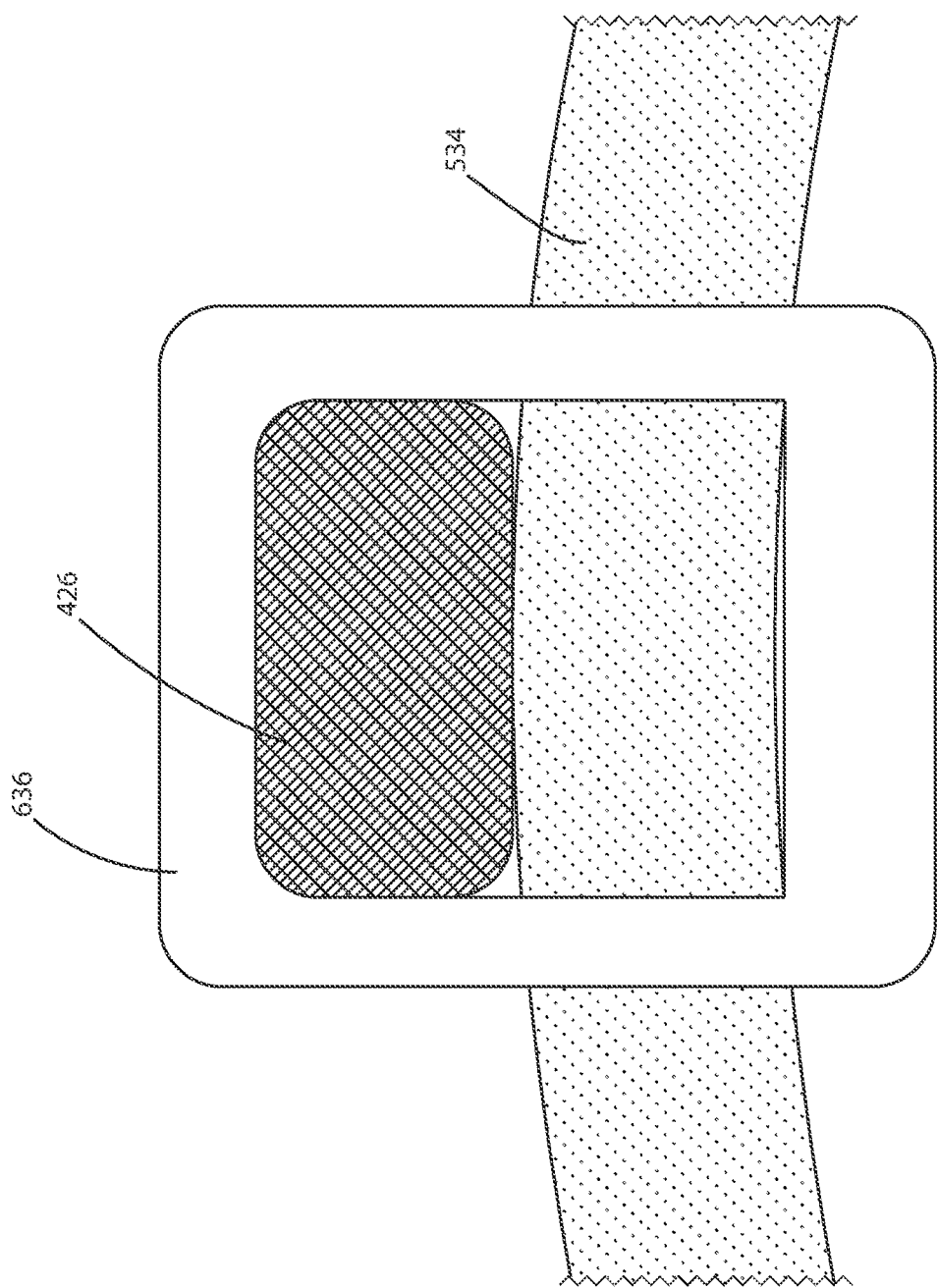
FIG. 8 is a cross-sectional schematic view of a web sutured to a frame taken along line 8-8' in FIG. 6 in accordance with various embodiments herein.

Referring now to FIG. 8, a cross-sectional schematic view of a web 534 sutured to a frame 208 taken along line 8-8' in FIG. 6 is shown in accordance with various embodiments herein. In some embodiments, the web 534 can be attached to one or more struts 426 of the frame 208. A suture 636 can extend around a strut 426 and around a portion of the web 534 to secure the web 534 to the frame 208. In some embodiments, a suture 636 can extend through a portion of the web 534. In the uncoated or pre-coated state, the suture 636 can be exposed or uncovered.

Figure 9:
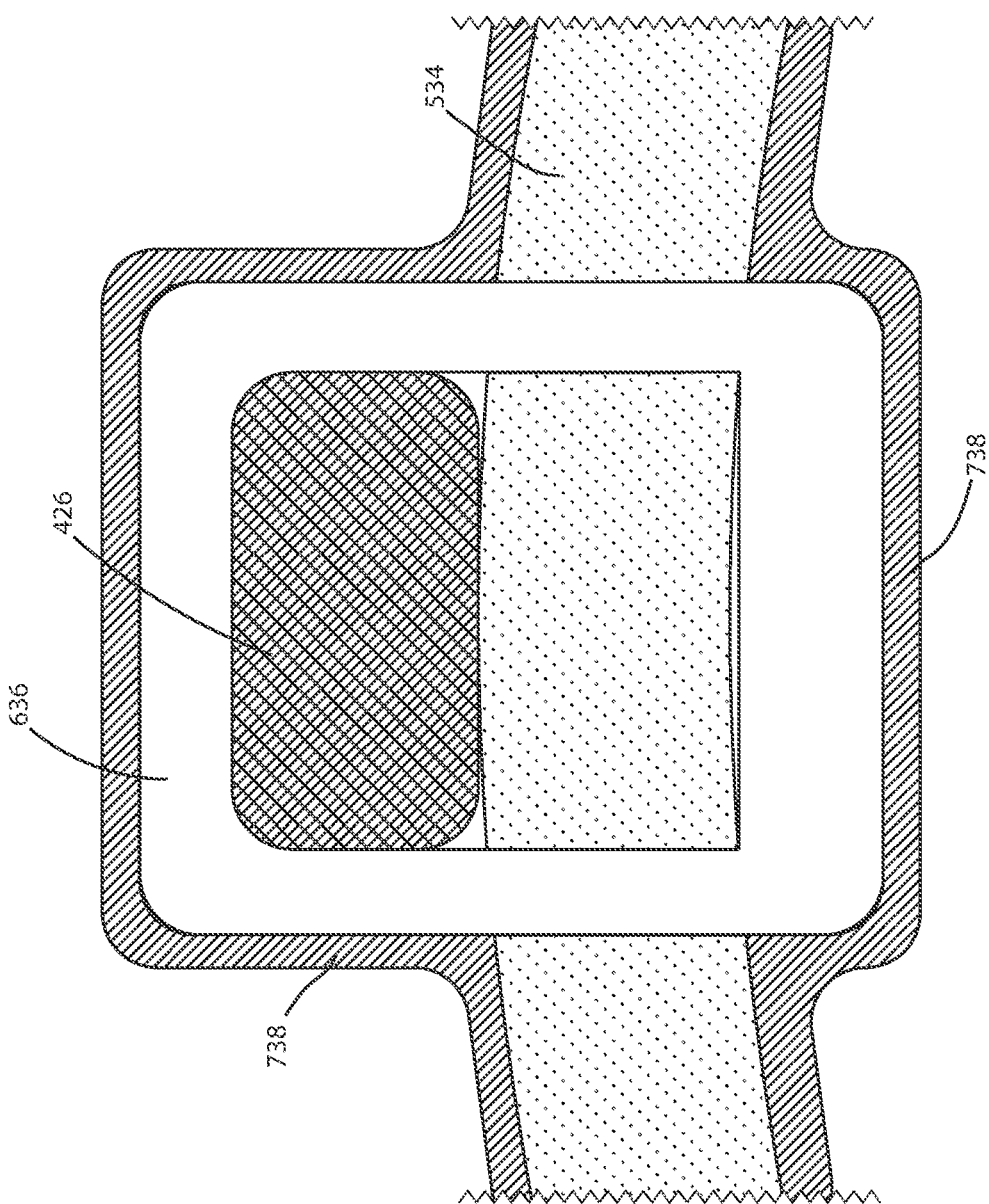
FIG. 9 is a cross-sectional schematic view of a web sutured to a frame taken along line 9-9' in FIG. 7 in accordance with various embodiments herein.

Referring now to FIG. 9, a cross-sectional schematic view of a web 534 sutured to a frame 208 taken along line 9-9' in FIG. 7 is shown in accordance with various embodiments herein. FIG. 9 shows a cross-sectional schematic view of the web 534 sutured to the frame 208 after the coating 738 has been applied. In various embodiments, at least some of the plurality of sutures 636 are covered with the second polymer or coating 738. In various embodiments, all of the plurality of sutures 636 are covered with the coating 738. In various embodiments, the sutures 636 are enclosed within the coating 738. In various embodiments, the sutures 636 do not extend through or pass through the coating 738. In various embodiments, the sutures 636 do not extend through or pass through at least one layer of the coating 738.

Figure 10:
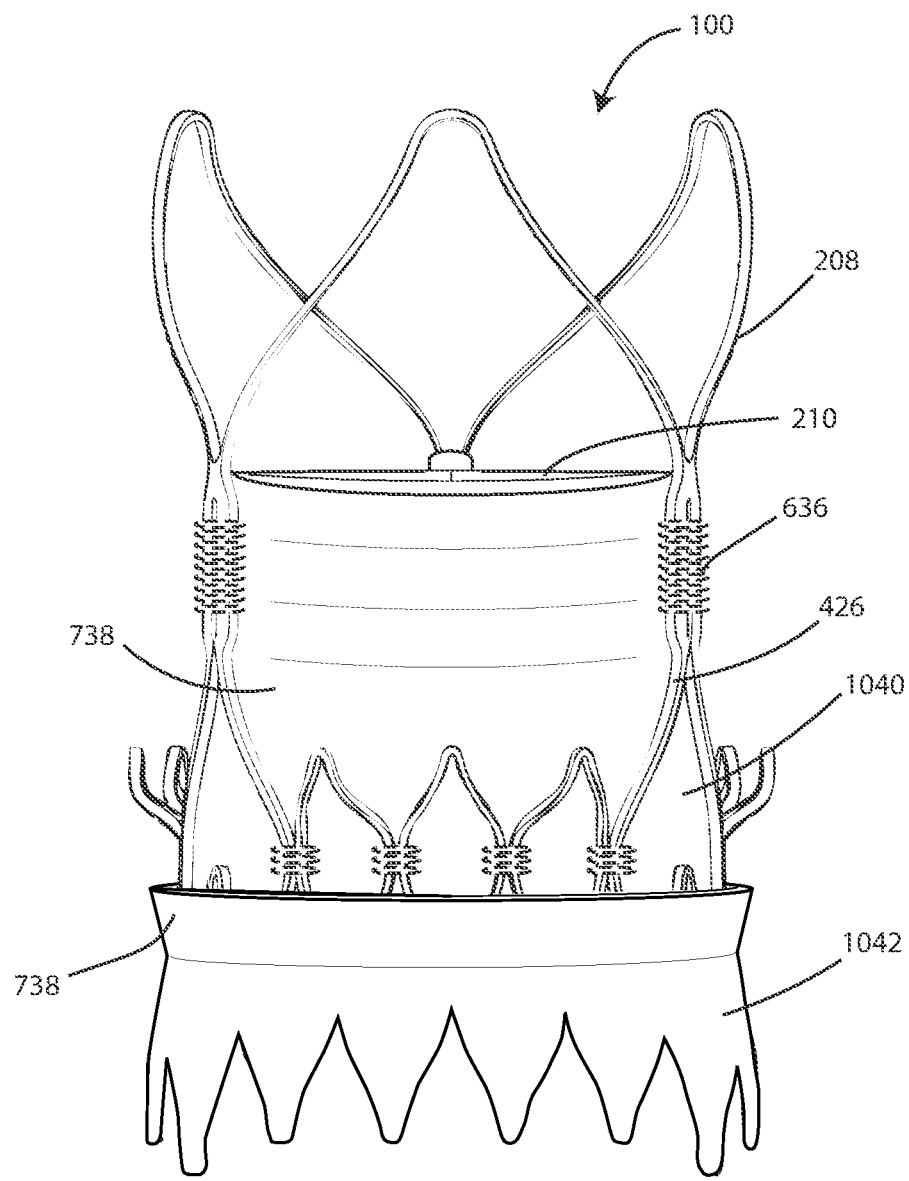
FIG. 10 is a front view of a prosthetic heart valve in accordance with various embodiments herein.

Referring now to FIG. 10, a front view of a prosthetic heart valve 100 is shown in accordance with various embodiments herein. The heart valve 100 can include a frame 208 and one or more valve leaflets 210. In some embodiments, the heart valve 100 also includes an inner skirt 1040. In some embodiments, the heart valve 100 also includes an outer sealing skirt 1042.

In various embodiments, the inner skirt 1040 can be attached to the frame 208 with a connection structure that does not pass through the coating, such as one or more sutures 636. In various embodiments, the outer sealing skirt 1042 can be attached to the frame 208 with a connection structure that does not pass through the coating, such as one or more sutures 636.

In various embodiments, the inner skirt 1040 can include a first polymer forming a porous support web 534, and a second polymer forming a coating 738 that can occlude pores in the porous support web 534. Similarly, in various embodiments, the outer sealing skirt 1042 can include the first polymer forming a porous support web 534, and the second polymer forming a coating 738 that can occlude pores in the porous support web 534.

In various embodiments, the web 534 can define various structural features of the valve 100. The web 534 can define at least one of a valve leaflet 210, an inner skirt 1040, and an outer sealing skirt 1042.

Figure 11:
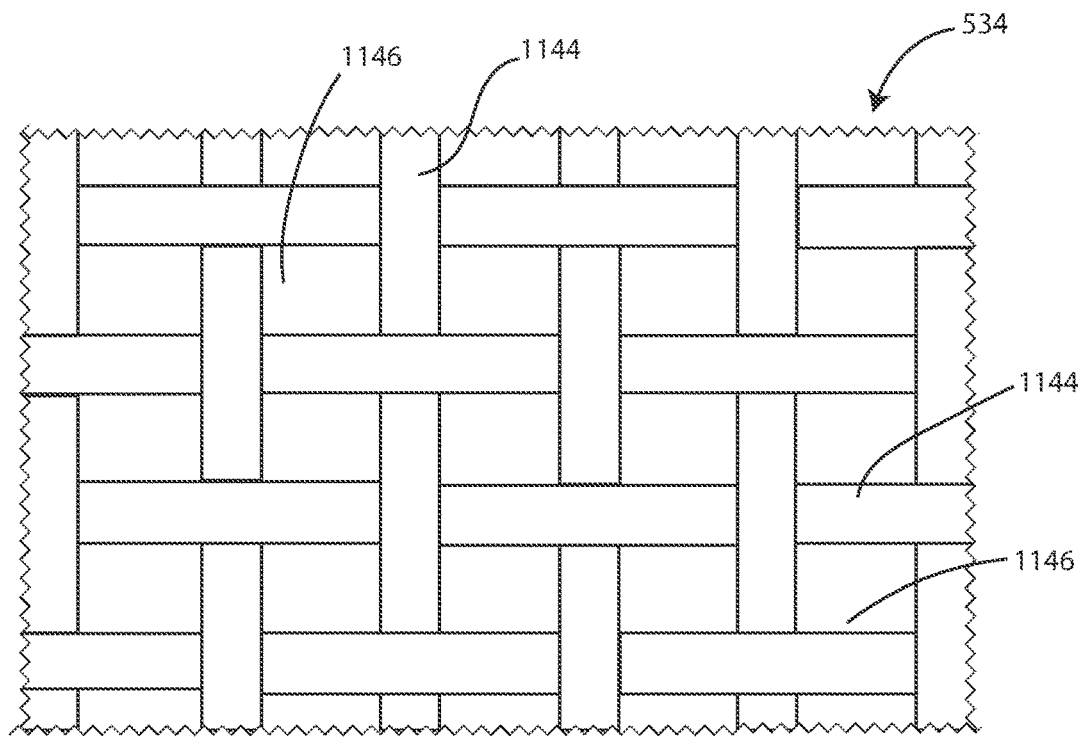
FIG. 11 is a view of a portion of a web in accordance with various embodiments herein.

Referring now to FIG. 11, a view of a portion of a web 534 is shown in accordance with various embodiments herein. FIG. 11 shows a porous web 534. In some embodiments, the porous web 534 can include a plurality of fibers 1144. The porous web 534 can define a plurality of pores 1146 between fibers 1144.

The web 534 shown in FIG. 11 can be a view of a portion of a web 534 prior to being coated. The uncoated web 534 can define pores 1146 which can allow for the coating to pass through the web 534. The coating can also surround individual fibers 1144, such as to attach the coating to the web 534.

Figure 12:
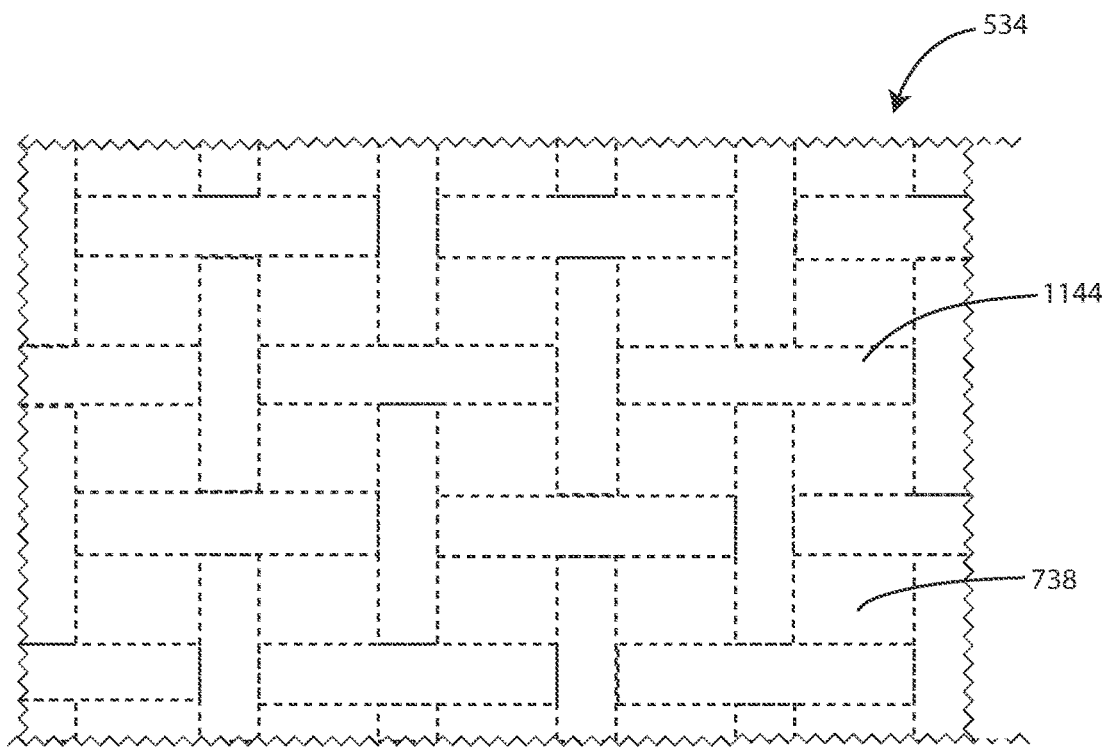
FIG. 12 is a view of a portion of a coated web in accordance with various embodiments herein.

The uncoated web in FIG. 11 can be coated with a polymeric coating 738. The coated web 534 is shown in FIG. 12. Referring now to FIG. 12, a view of a portion of a coated web 534 is shown in accordance with various embodiments herein.

In various embodiments, the coating 738 can occlude the pores of the web 534, as shown in FIG. 12. The pores 1146 can be occluded such that liquid, such as blood, cannot pass through the web 534 and coating 738. In addition to the pores 1146 being occluded, the fibers 1144 can be coated, such that at least some of the fibers 1144 can be covered or enclosed within the coating 738. In some embodiments, all of the fibers 1144 of the web are covered or enclosed within the coating 738.

Figure 13:
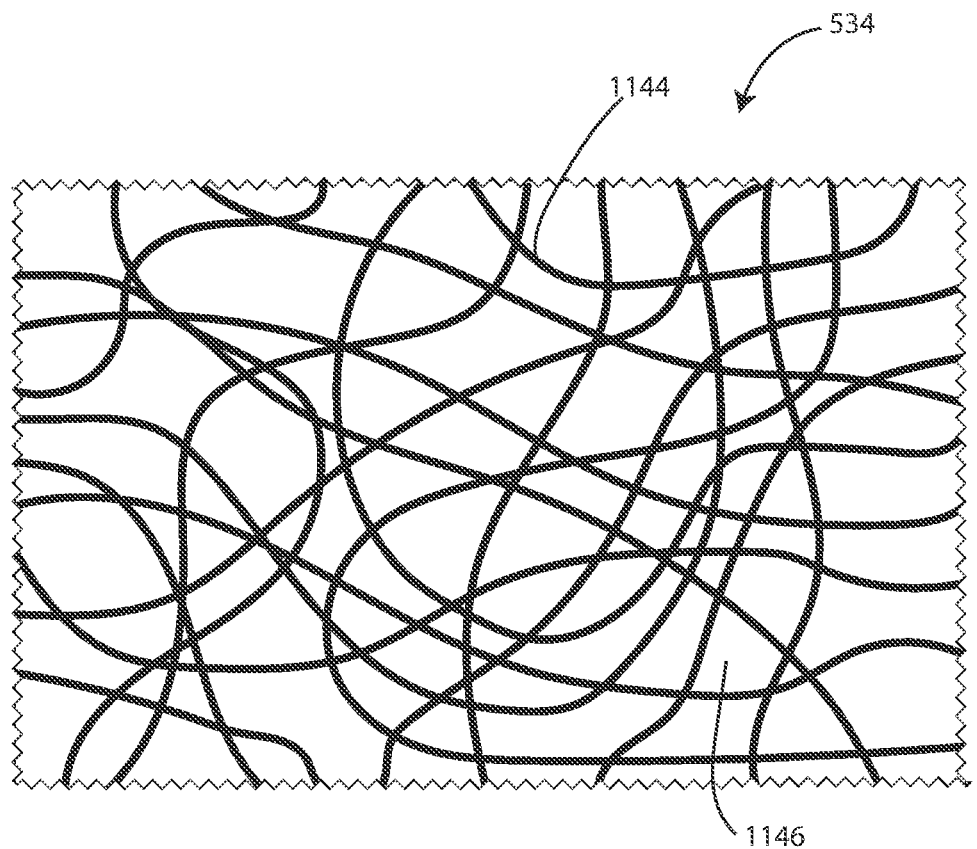
FIG. 13 is a view of a portion of a web in accordance with various embodiments herein.

FIGS. 11 and 12 show a web 534 with organized fibers 1144, such as fibers 1144 that are in a repeating layout or pattern. However, in some embodiments, the fibers 1144 can be unorganized or random, such as shown in FIG. 13. Referring now to FIG. 13, a view of a portion of a web 534 is shown in accordance with various embodiments herein. FIG. 13 shows a porous web 534 including unorganized fibers 1144 (or randomly oriented fibers). The unorganized fibers 1144 can be random, such as having varying lengths, shapes, and positions. The pores 1146 can also have random or various shapes and sizes as a result of the unorganized fibers 1144. In some embodiments, the unorganized fibers can be electrospun fibers.

Figure 14:
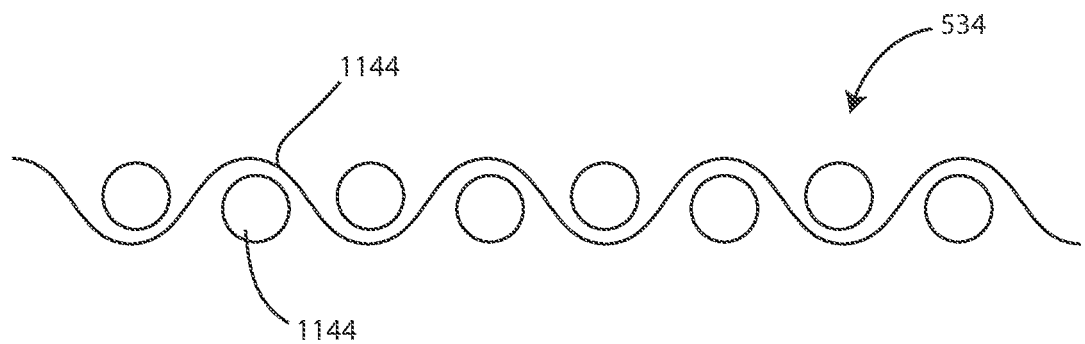
FIG. 14 is a schematic side view of a portion of a single layer web in accordance with various embodiments herein.
Figure 15:
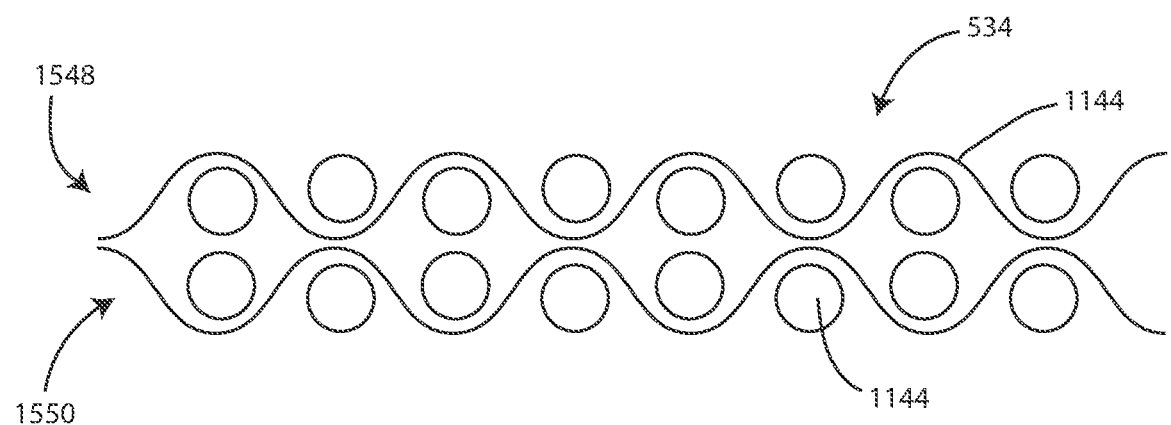
FIG. 15 is a schematic side view of a portion of a double layer web in accordance with various embodiments herein.

In some cases, webs herein can be formed of various numbers of layers. Referring now to FIG. 14, a cross-sectional schematic side view of a portion of a single layer web 534 is shown in accordance with various embodiments herein. FIG. 14 shows a porous web 534 including fibers 1144 in a woven configuration. Referring now to FIG. 15, a cross-sectional schematic side view of a portion of a double layer web 534 is shown in accordance with various embodiments herein. FIG. 15 shows a porous web 534 including a first layer 1548 and a second layer 1550. Each layer 1548, 1550 includes fibers 1144 in a woven configuration. In some embodiments, the webs herein can include 1, 2, 3, 4, 5, 6, 7, 8, 9, 10, 12, 15, 20, or 30 layers, or a number of layers falling within a range between any of the foregoing.

In some embodiments, a single layer web 534, such as shown in FIG. 14, can have thickness of at least 0.1 mm, 0.25 mm, 0.5 mm, 1 mm, 2 mm, or 5 mm. In various embodiments, the single layer web 534 can have a thickness of less than 10 mm, 5 mm, 4 mm, 3 mm, 2 mm, or 1 mm. It should be understood that the thickness of the web 534 can fall within a range between any combination of the thicknesses listed above. It should also be understood that the first layer 1548 and the second layer 1550 can have the same thicknesses as the single layer web 534 shown in FIG. 14. In some embodiments, the first layer 1548 and the second layer 1550 can be substantially the same, such as having the same thickness and general construction. In some embodiments, the double layer web 534 shown in FIG. 15 can have a thickness that is twice the thickness of the single layer web 534 shown in FIG. 14.

Figure 16:
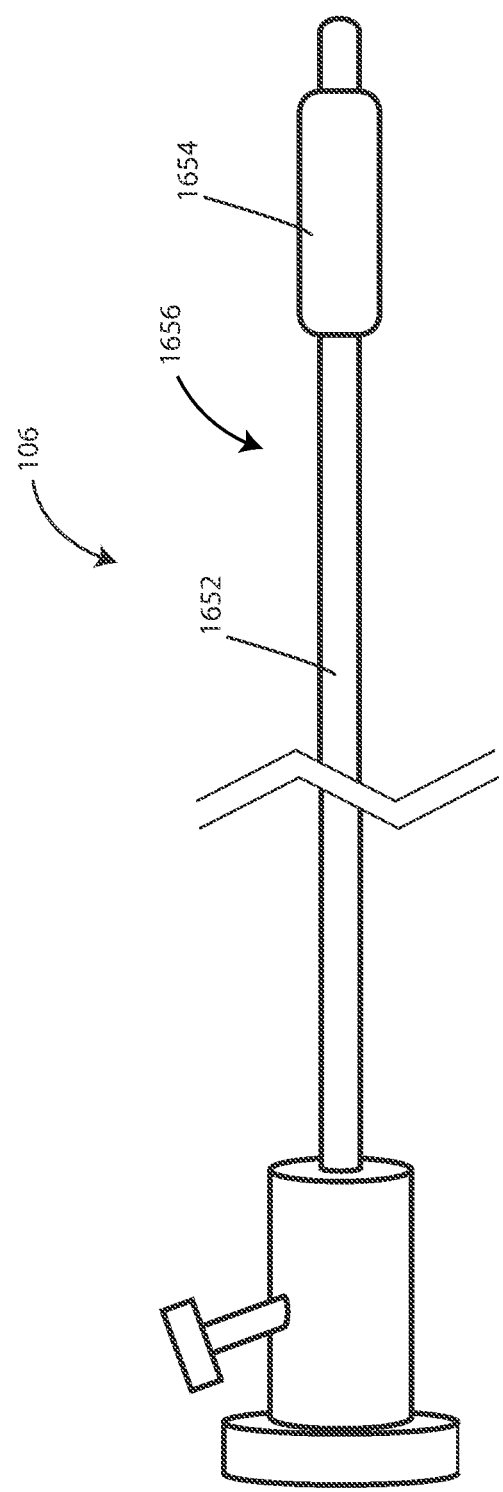
FIG. 16 is a schematic view of a delivery catheter in accordance with various embodiments herein.

Referring now to FIG. 16, a schematic view of a delivery catheter 106 is shown in accordance with various embodiments herein. In some embodiments, a heart valve replacement system can include a delivery catheter 106. The delivery catheter 106 can include a shaft 1652. The delivery catheter 106 can include a heart valve accommodation region 1656. The heart valve accommodation region 1656 can be configured to receive a heart valve. The delivery catheter 106 can also include a balloon 1654. In some embodiments, the balloon 1654 is distal relative to the heart valve accommodation region 1656. In some embodiments, the balloon 1654 forms a part of the heart valve accommodation region 1656. In some embodiments, the delivery catheter 106 can be configured as a transfemoral delivery catheter. While FIG. 16 depicts a balloon catheter, it will be appreciated that in some embodiments a delivery catheter herein may not include a balloon. In some embodiments, a frame of the heart valve can be self-expanding. In some embodiments, other mechanical devices can be used to expand the heart valve into position. In some embodiments, a frame of the heart valve can be non-expandable.

Webs

Various embodiments herein include heart valves having a frame and a web attached thereto, onto which a polymer can be applied.

In some embodiments, the web can specifically include a fibrous web. In some embodiments, the web can include oriented and/or non-oriented fibers. In some embodiments, the web can include a textile, such as a woven or non-woven textile. In some embodiments, the web can include a mesh. In some embodiments, the web can exist as a single layer. In some embodiments, the web can exist as a plurality of layers, such as 2, 3, 4, 5, 6 or more layers, or a number of layers falling within a range between any of the foregoing.

The web can be formed of various materials. In some embodiments, the web can be formed of fibers including a metal, a polymer (synthetic or natural), a glass, or the like. In some embodiments, the web can specifically include fibers including a thermoplastic polymer. In some embodiments, the web can specifically include fibers including polyethylene terephthalate. However, in some embodiments, the web can include one or more thermoset polymers. In some embodiment, the web can be formed from homopolymers and/or copolymers.

In some embodiments, exemplary webs herein can include an electrospun substrate. In some embodiments, the electrospun substrate can correspond to at least one valve leaflet. In some embodiments, the electrospun substrate can include fibers formed of a polyisobutylene urethane (PIB-PUR) copolymer, polyether-polyurethane copolymers (PE-PUR), a polyamide, a polyester, or polyethylene.

Applied Coating Materials

Various embodiments herein include materials (including, but not limited to polymers) that are applied onto webs in order to form components of heart valves. In various embodiments, the applied polymer can be applied from a solution or mixture including one or more polymers and one or more solvents. The amount of the polymer in the mixture (or in some cases solution) with the solvent can vary. In some embodiments, the amount of polymer can be about 1, 2, 3, 5, 10, 15, 20, 25, 30, 40, 50, 60, 70, or more percent by weight, or an amount falling within a range between any of the foregoing. However, in some embodiment, the applied polymer can be applied in the form of a composition lacking a solvent.

In various embodiments, the applied polymer can be applied in a flowable form, allowing for the ingress of the polymer into pores of the web. Applied polymers herein can include both thermoplastics and thermosets. Applied polymers herein can include homopolymers and copolymers. Applied polymers herein can include elastomers and non-elastomeric polymers. Applied polymers herein can include curable polymers. Applied polymers herein can include UV-curable polymers. Applied polymers herein can include, but are not limited to, polysiloxanes (silicones), polyurethanes, polyesters, polybutadiene, polyethylene terephthalate, parylene, polyolefins (including polyethylenes and polypropylenes), polyisoprene, polystyrene, polyvinyl alcohol, polyvinylpyrrolidone, polyvinylchloride, acrylonitrile butadiene styrene, ethylene vinyl acetate, cellulosic polymers, and the like.

Methods

Many different methods are contemplated herein, including, but not limited to, methods of making, methods of using, and the like. Aspects of system/device operation described elsewhere herein can be performed as operations of one or more methods in accordance with various embodiments herein.

Figure 17:
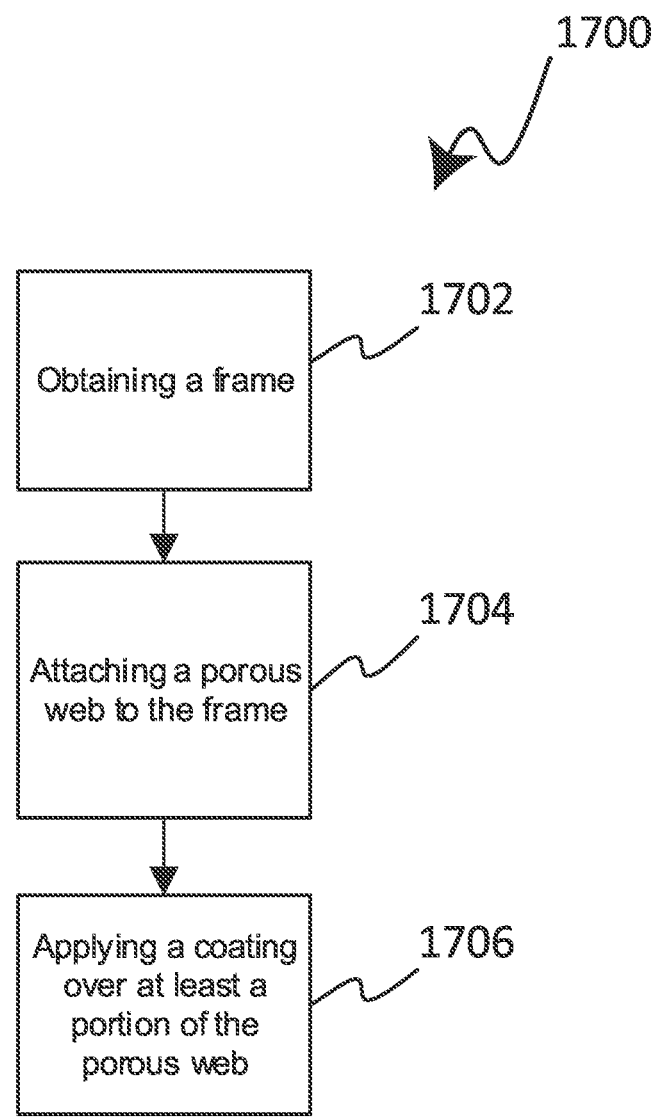
FIG. 17 is a schematic of operations of a method of manufacturing a heart valve in accordance with various embodiments herein.

Referring now to FIG. 17, a flowchart depicting a method 1700 of manufacturing a heart valve is shown in accordance with various embodiments herein. In some embodiments, the method 1700 of manufacturing a heart valve includes obtaining a frame 1702, attaching a porous web to the frame 1704, and applying a coating over at least a portion of the porous web 1706. In some embodiments, applying a coating can include a polymeric coating. In some embodiments, applying a coating can be repeated one or more times to results in multiple coats. In some embodiments, drying and/or curing steps can occur between the application of coats. In some embodiments, attaching the porous web to the frame 1702 can include suturing the porous web to the frame. In various embodiments, the porous web can define at least one valve leaflet. In various embodiments, the porous web can include polyethylene terephthalate.

In some embodiments, applying a coating over the porous web can occlude pores within the porous web. In some embodiments, applying the coating over the porous web can include coating a plurality of sutures attaching the porous web to the frame. In various embodiments, applying a coating over the porous web comprises dip coating the coating onto the porous web. In various embodiments, applying a coating over the porous web comprises spray coating the coating onto the porous web. In various embodiments, applying a coating over the porous web comprises vapor depositing the coating onto the porous web. In some embodiments, the method can further include attaching an electrospun substrate to the frame. In some embodiments, the method can further include attaching an electrospun substrate to an existing portion of a substrate. In various embodiments, the electrospun substrate corresponds to at least one valve leaflet. In various embodiments, the electrospun substrate comprises a polyisobutylene urethane (PIB-PUR) copolymer.

Figure 18:
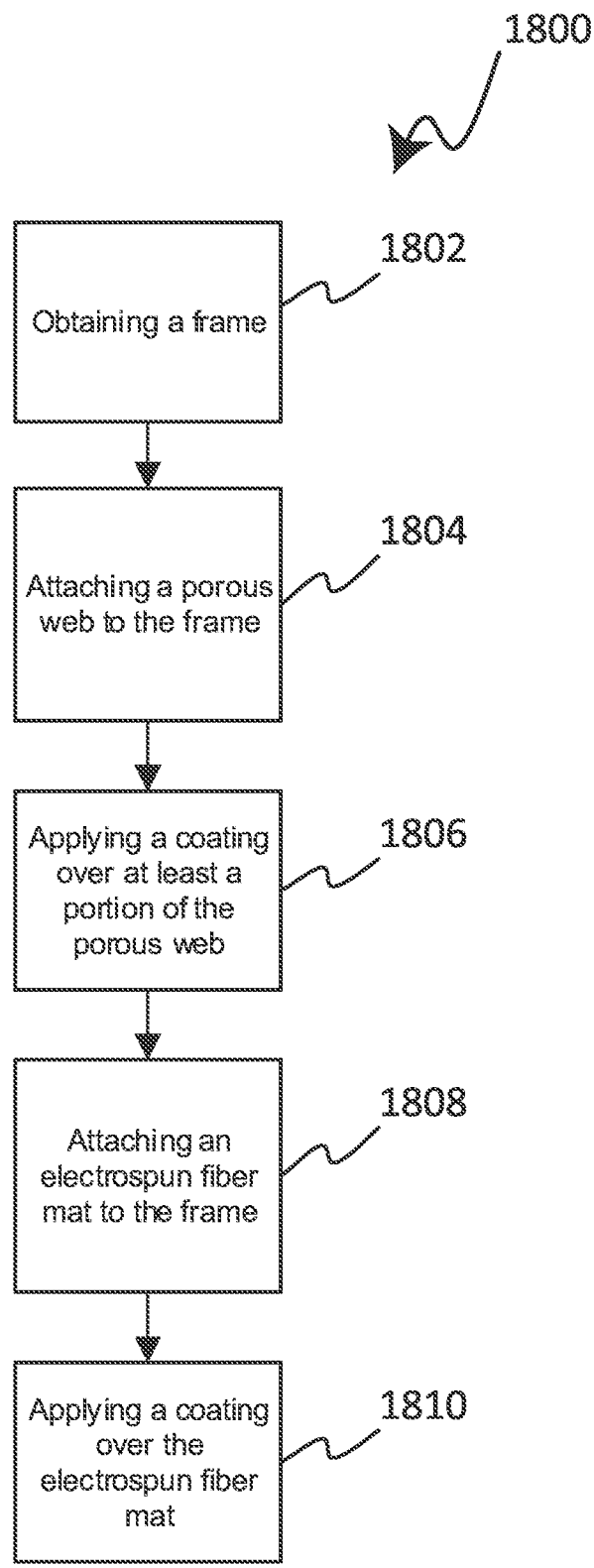
FIG. 18 is a schematic of operations of a method of manufacturing a heart valve in accordance with various embodiments herein.

Referring now to FIG. 18, a flow chart depicting a method 1800 of manufacturing a heart valve is shown in accordance with various embodiments herein. The method 1800 can include obtaining a frame 1802, attaching a porous web to the frame 1804. The method 1800 can include applying a coating over at least a portion of the porous web 1806. The method 1800 can further include attaching an electrospun fiber mat to the frame 1808 and/or to the porous web 1806. The method 1800 can further include applying a coating over the electrospun fiber mat 1810 and, in some embodiments, over at least a portion of the porous web (e.g. if not already applied to the porous web).

Figure 19:
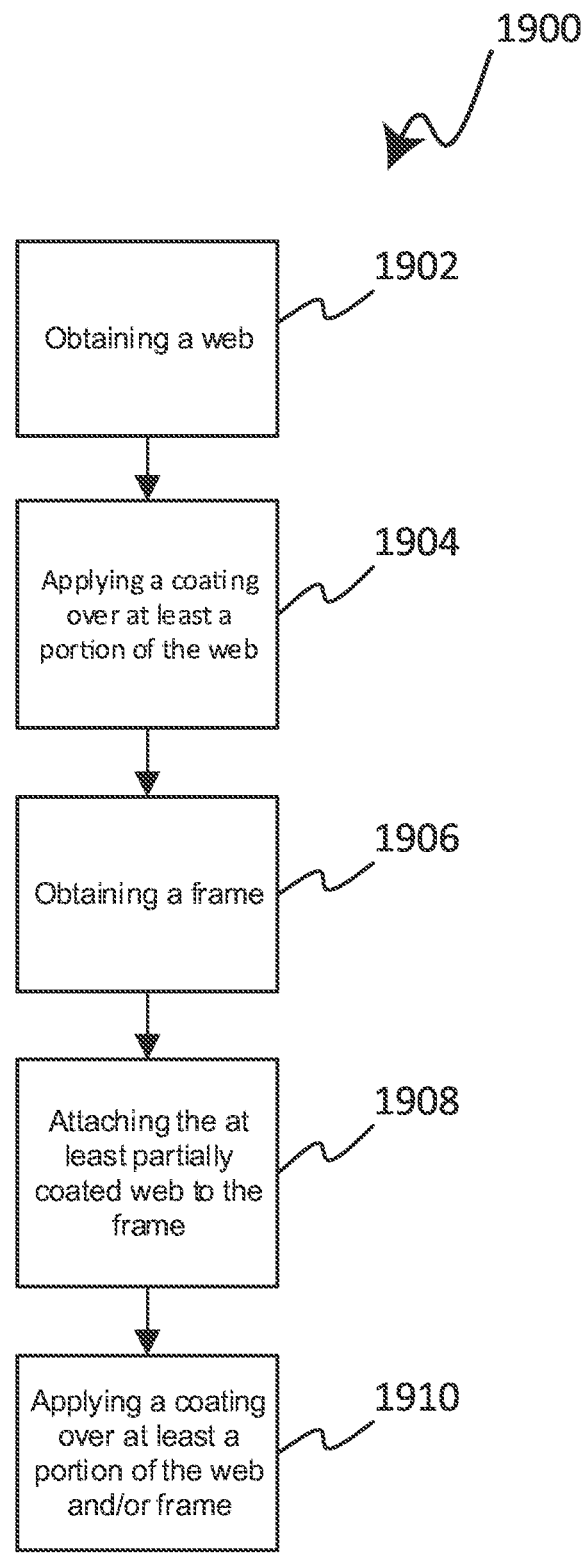
FIG. 19 is a schematic of operations of a method of manufacturing a heart valve in accordance with various embodiments herein.

Referring now to FIG. 19, a flow chart depicting a method 1900 of manufacturing a heart valve is shown in accordance with various embodiments herein. The method 1900 can include obtaining a web 1902, such as a shaped web. The method 1900 can further include applying a coating over at least a portion of the web 1904. The method 1900 can further include obtaining a frame 1906. The method 1900 can further include attaching the at least partially coated web to the frame 1908. The method 1900 can further include applying a coating over at least a portion of the web and/or frame 1910.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A method of manufacturing a heart valve comprising:
obtaining a frame;
attaching a porous web to the frame with a plurality of attachment elements;
applying a coating over at least a portion of the porous web, which is attached to the frame, and at least a portion of the plurality of attachment elements, which attach the porous web to the frame, to form an inner skirt and a plurality of leaflets;
wherein the attachment elements do not pass through the coating on the porous web.

2. The method of claim 1, wherein the porous web comprises a mesh.

3. The method of claim 1, wherein attaching the porous web to the frame comprises suturing the porous web to the frame.

4. The method of claim 3, wherein the plurality of attachment elements comprises a plurality of sutures.

5. The method of claim 1, wherein applying the coating over the porous web occludes pores within the porous web.

6. The method of claim 1, wherein the porous web defines at least one valve leaflet.

7. The method of claim 1, wherein the porous web comprises an electrospun substrate.

8. The method of claim 7, wherein the electrospun substrate corresponds to at least one valve leaflet.

9. The method of claim 7, wherein the electrospun substrate comprises a polyisobutylene urethane (PIB-PUR) copolymer and the porous web comprises polyethylene terephthalate.

10. The method of claim 1, wherein the coating is applied to the frame and the attachment elements at the same time.

11. The method of claim 1, wherein the coating occludes the pores in the porous web such that fluids are unable to pass through the coated porous web.

12. The method of claim 1, wherein the entire porous web and frame are covered in the coating.

13. A method of manufacturing a heart valve comprising:
obtaining a frame;
attaching a porous web to the frame with a plurality of attachment elements; and
applying a coating over at least a portion of the porous web, which is attached to the frame, and at least a portion of the plurality of attachment elements, which attach the porous web to the frame, to form an inner skirt and a plurality of leaflets;
wherein the coating is applied to the frame and the attachment elements at the same time.

14. The method of claim 13, wherein attaching the porous web to the frame comprises suturing the porous web to the frame.

15. The method of claim 14, wherein the plurality of attachment elements comprises a plurality of sutures.

16. The method of claim 13, wherein applying a coating over the porous web occludes pores within the porous web.

17. A method of manufacturing a heart valve comprising:
obtaining a frame;
attaching a porous web to the frame with a plurality of attachment elements; and
applying a coating over at least a portion of the porous web, which is attached to the frame, and at least a portion of the plurality of attachment elements, which attach the porous web to the frame, to form an inner skirt and a plurality of leaflets;
wherein the porous web comprises an electrospun substrate, wherein the electrospun substrate comprises a polyisobutylene urethane (PIB-PUR) copolymer and the porous web comprises polyethylene terephthalate.

* * * * *